US012589247B2

(12) United States Patent
Single et al.

(10) Patent No.: US 12,589,247 B2
(45) Date of Patent: Mar. 31, 2026

(54) POWER EFFICIENT STIMULATORS

(71) Applicant: Saluda Medical Pty Ltd, Level (AU)

(72) Inventors: Peter Scott Vallack Single, Artarmon (AU); James Hamilton Wah, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 394 days.

(21) Appl. No.: 18/295,828

(22) Filed: Apr. 4, 2023

(65) Prior Publication Data

US 2023/0233859 A1     Jul. 27, 2023

Related U.S. Application Data

(63) Continuation of application No. 16/969,886, filed as application No. PCT/AU2019/050116 on Feb. 15, 2019, now Pat. No. 11,633,602.

(30) Foreign Application Priority Data

Feb. 15, 2018     (AU) ................................. 2018900480

(51) Int. Cl.
*A61N 1/36*          (2006.01)
*A61N 1/378*         (2006.01)

(52) U.S. Cl.
CPC ..... *A61N 1/36125* (2013.01); *A61N 1/36132* (2013.01); *A61N 1/36196* (2013.01); *A61N 1/3787* (2013.01)

(58) Field of Classification Search
CPC ............ A61N 1/36125; A61N 1/36132; A61N 1/36196; A61N 1/3787; A61N 1/0551;
(Continued)

(56) References Cited

U.S. PATENT DOCUMENTS 4,856,525 A     8/1989   Van den Honert
5,895,416 A     4/1999   Barreras et al.
(Continued)

FOREIGN PATENT DOCUMENTS

WO          9414376 A1      7/1994
WO          9417855 A1      8/1994
(Continued)

OTHER PUBLICATIONS

International Preliminary Report on Patentability for International Application No. PCT/AU2019/050116, Issued Aug. 18, 2020, 10 pgs.
(Continued)

*Primary Examiner* — Paula J Stice
(74) *Attorney, Agent, or Firm* — Barnes & Thornburg LLP

(57) ABSTRACT

This disclosure relates to a device for applying a neural stimulus. A battery supplies electrical energy at a battery voltage and an electrode applies the electrical energy to neural tissue. A circuit measures the nervous response of the tissue and a voltage converter receives the electrical energy from the battery and controls a voltage applied to the electrode based on the measured nervous response of the tissue. This direct voltage control is energy efficient because losses across a typical current mirror are avoided. Further, the control based on the measured nervous response leads to automatic compensation of impedance variation due to in-growth or change in posture. As a result, the stimulation results in a desired neural response.

16 Claims, 15 Drawing Sheets

(58) Field of Classification Search
CPC ............ A61N 1/36067; A61N 1/36071; A61N 1/36075; A61N 1/36139; A61N 1/36135; A61N 1/36062
See application file for complete search history.

(56) References Cited

U.S. PATENT DOCUMENTS

| | | | |
|---|---|---|---|
| 7,127,298 | B1 | 10/2006 | He et al. |
| 7,941,713 | B2 | 5/2011 | Chang et al. |
| 8,712,547 | B2 | 4/2014 | Whitehurst et al. |
| 9,031,664 | B2 | 5/2015 | Trier |
| 9,079,041 | B2 | 7/2015 | Park et al. |
| 9,283,394 | B2 | 3/2016 | Whitehurst et al. |
| 9,421,371 | B2 | 8/2016 | Pless et al. |
| 10,183,168 | B2 | 1/2019 | Baru et al. |
| 10,543,362 | B2 | 1/2020 | Peterson |
| 11,298,536 | B2 | 4/2022 | Wu et al. |
| 11,364,378 | B2 | 6/2022 | Parramon et al. |
| 2008/0051647 | A1 | 2/2008 | Wu et al. |
| 2013/0338732 | A1* | 12/2013 | Foutz ................. A61N 1/36125 607/2 |
| 2014/0228905 | A1 | 8/2014 | Bolea |
| 2015/0360031 | A1 | 12/2015 | Bornzin et al. |
| 2016/0287182 | A1 | 10/2016 | Single |
| 2017/0296823 | A1 | 10/2017 | Hershey et al. |
| 2018/0161573 | A1 | 6/2018 | Carbunaru |
| 2019/0255333 | A1 | 8/2019 | Baru et al. |
| 2021/0178162 | A1 | 6/2021 | Boor et al. |
| 2021/0393962 | A1 | 12/2021 | Durand |
| 2023/0158307 | A1 | 5/2023 | Weiss et al. |

FOREIGN PATENT DOCUMENTS

| | | | |
|---|---|---|---|
| WO | 9912607 | A1 | 3/1999 |
| WO | 0209808 | A1 | 2/2002 |
| WO | 2006121424 | A2 | 11/2006 |
| WO | 2007008212 | A1 | 1/2007 |
| WO | 2008004204 | A1 | 1/2008 |
| WO | 2008048725 | A1 | 4/2008 |
| WO | 2008049199 | A1 | 5/2008 |
| WO | 2010051317 | A1 | 5/2010 |
| WO | 2010062517 | A1 | 6/2010 |
| WO | 2013002991 | A1 | 1/2013 |
| WO | 2013138252 | A1 | 9/2013 |
| WO | 2013115643 | A3 | 10/2013 |
| WO | 2012103519 | A3 | 3/2014 |
| WO | 2014071445 | A1 | 5/2014 |
| WO | 2014071446 | A1 | 5/2014 |
| WO | 2014137861 | A1 | 9/2014 |
| WO | 2014169145 | A1 | 10/2014 |
| WO | 2016090436 | A1 | 6/2016 |
| WO | 2016191055 | A1 | 12/2016 |
| WO | 2017011305 | A1 | 1/2017 |
| WO | 2017116760 | A1 | 7/2017 |
| WO | 2017219096 | A1 | 12/2017 |
| WO | 2018048909 | A1 | 3/2018 |
| WO | 2018048916 | A1 | 3/2018 |
| WO | 2018048917 | A1 | 3/2018 |
| WO | 2018048920 | A1 | 3/2018 |
| WO | 2019152553 | A1 | 8/2019 |
| WO | 2019157559 | A1 | 8/2019 |
| WO | 2019190678 | A1 | 10/2019 |
| WO | 2019209595 | A1 | 10/2019 |
| WO | 2020082118 | A1 | 4/2020 |
| WO | 2020082128 | A1 | 4/2020 |
| WO | 2020205170 | A1 | 10/2020 |
| WO | 2020236829 | A1 | 11/2020 |
| WO | 2021015917 | A1 | 1/2021 |
| WO | 2021046120 | A1 | 3/2021 |
| WO | 2021102448 | A1 | 5/2021 |
| WO | 2021108428 | A1 | 6/2021 |
| WO | 2021155326 | A1 | 8/2021 |
| WO | 2018013884 | A9 | 9/2021 |
| WO | 2021178026 | A1 | 9/2021 |
| WO | 2021178207 | A1 | 9/2021 |
| WO | 2021216666 | A1 | 10/2021 |
| WO | 2021216680 | A1 | 10/2021 |
| WO | 2022072106 | A1 | 4/2022 |
| WO | 2022109514 | A1 | 5/2022 |
| WO | 2022197748 | A1 | 9/2022 |
| WO | 2022251519 | A3 | 1/2023 |
| WO | 2023028646 | A1 | 3/2023 |
| WO | 2023059487 | A1 | 4/2023 |
| WO | 2023076904 | A1 | 5/2023 |

OTHER PUBLICATIONS

International Search Report and Written Opinion for International Application No. PCT/AU2019/050116, Search completed May 10, 2019, Mailed May 10, 2019, 24 Pgs.
Laird-Wah, "Improving Spinal Cord Stimulation: Model-Based Approaches to Evoked Response Telemetry", UNSW Thesis, Aug. 2015, 279 pgs.
Peterson et al., "Stimulation artifact rejection in closed-loop, distributed neural interfaces", ESSCIRC, 42nd European Solid-State Circuits Conference, Lausanne, 2016, pp. 233-235.

* cited by examiner

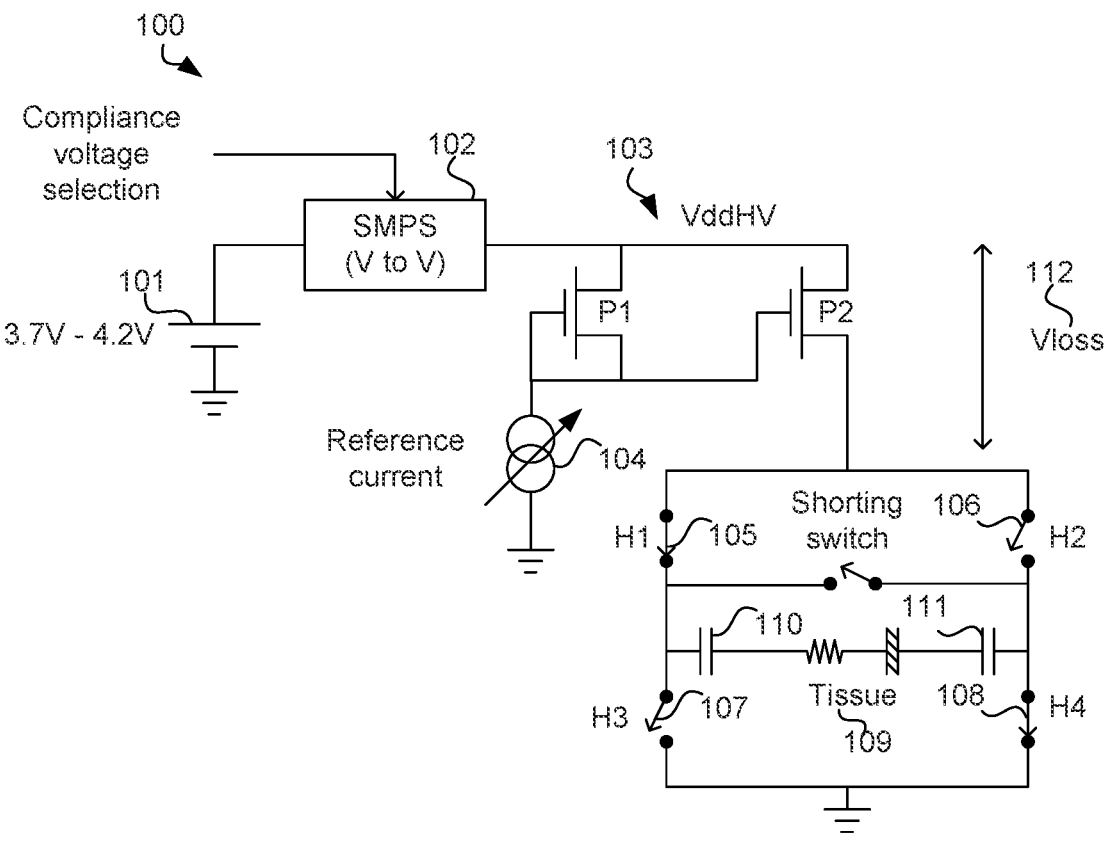
Fig. 1
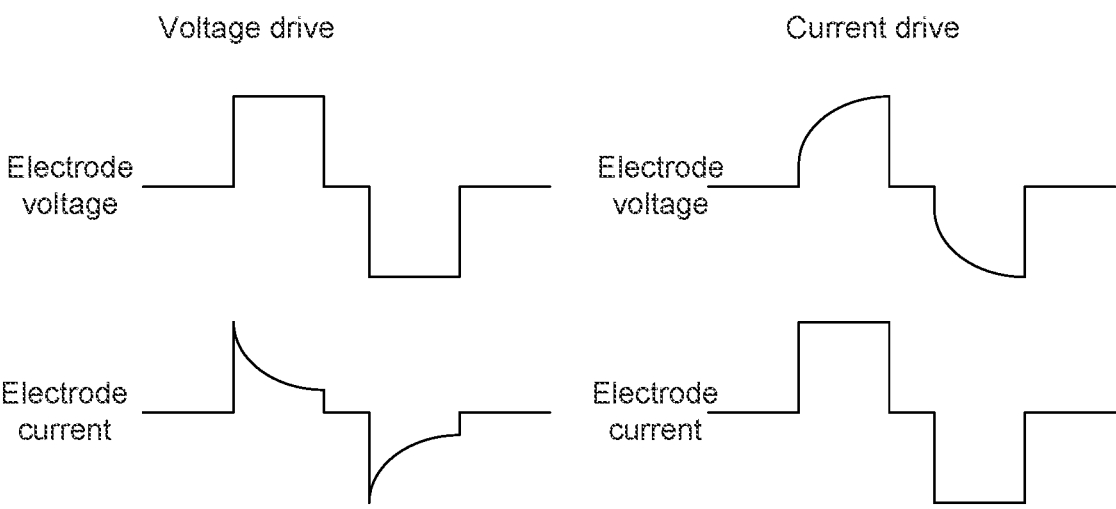
Fig. 2a                                          Fig. 2b

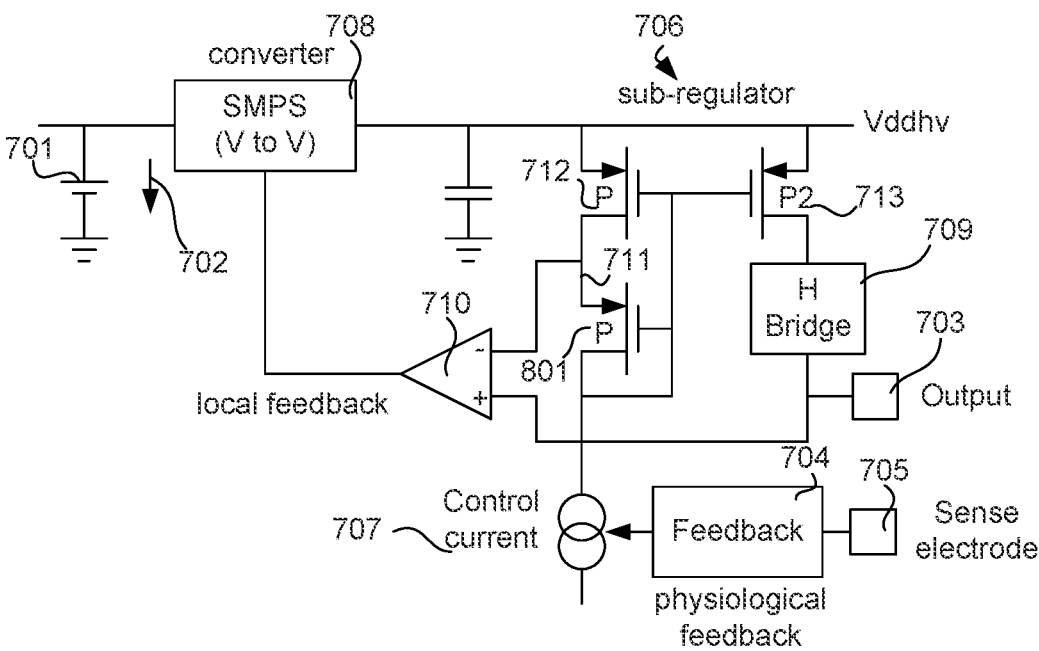
Fig. 8
900
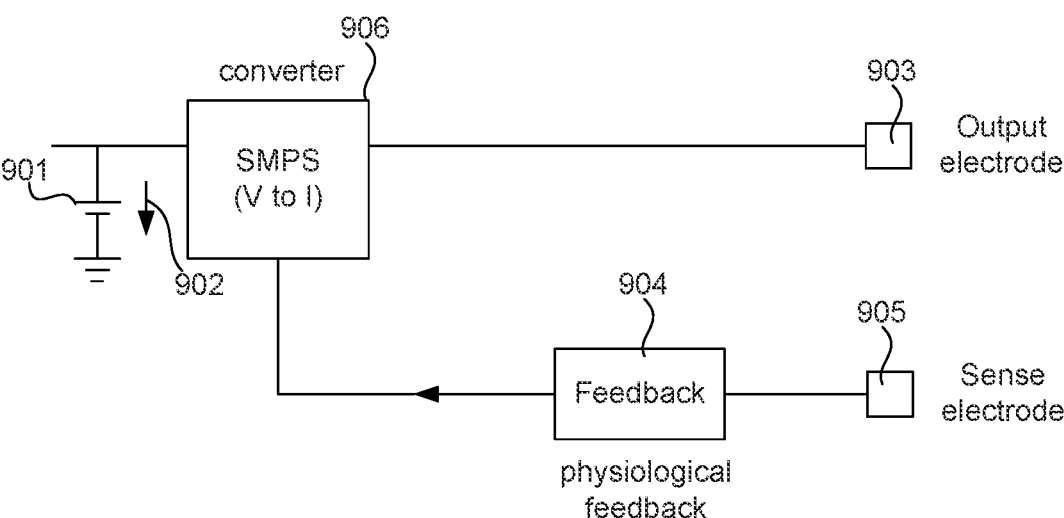
Fig. 9

1200

1206

$I = \dfrac{V_i}{R}$

1300

1400

External control

M    Const. $V_P$    $V_2$ $V_I$     Const. $V_P$    $V_1$ $V_I$

1401

Multiplying Voltage Controlled Delay MVCD    1405    Voltage Controlled Delay VCD    1402

Inductor control voltage 1404    1403

Pulse width inversely proportional to battery voltage

Frequency proportional to tissue voltage and external control

1500

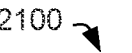
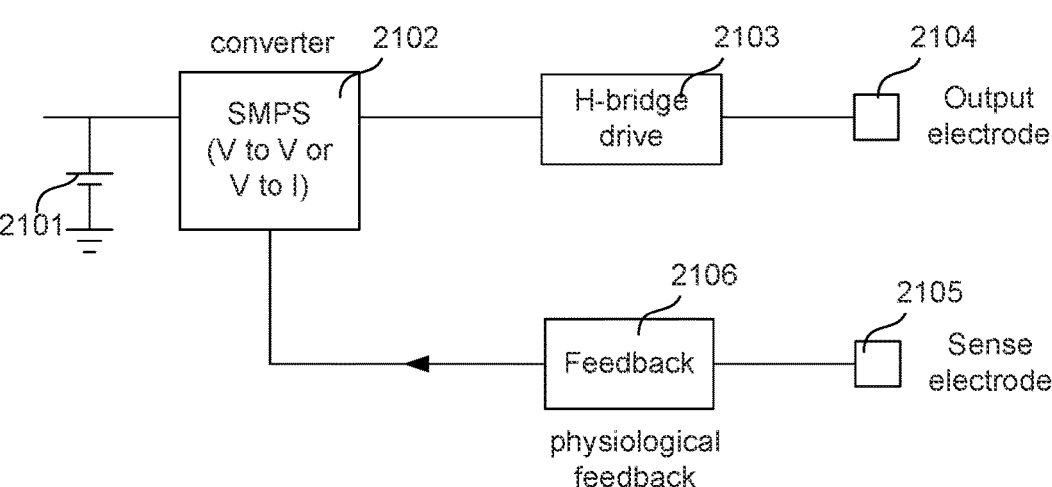
Fig. 21
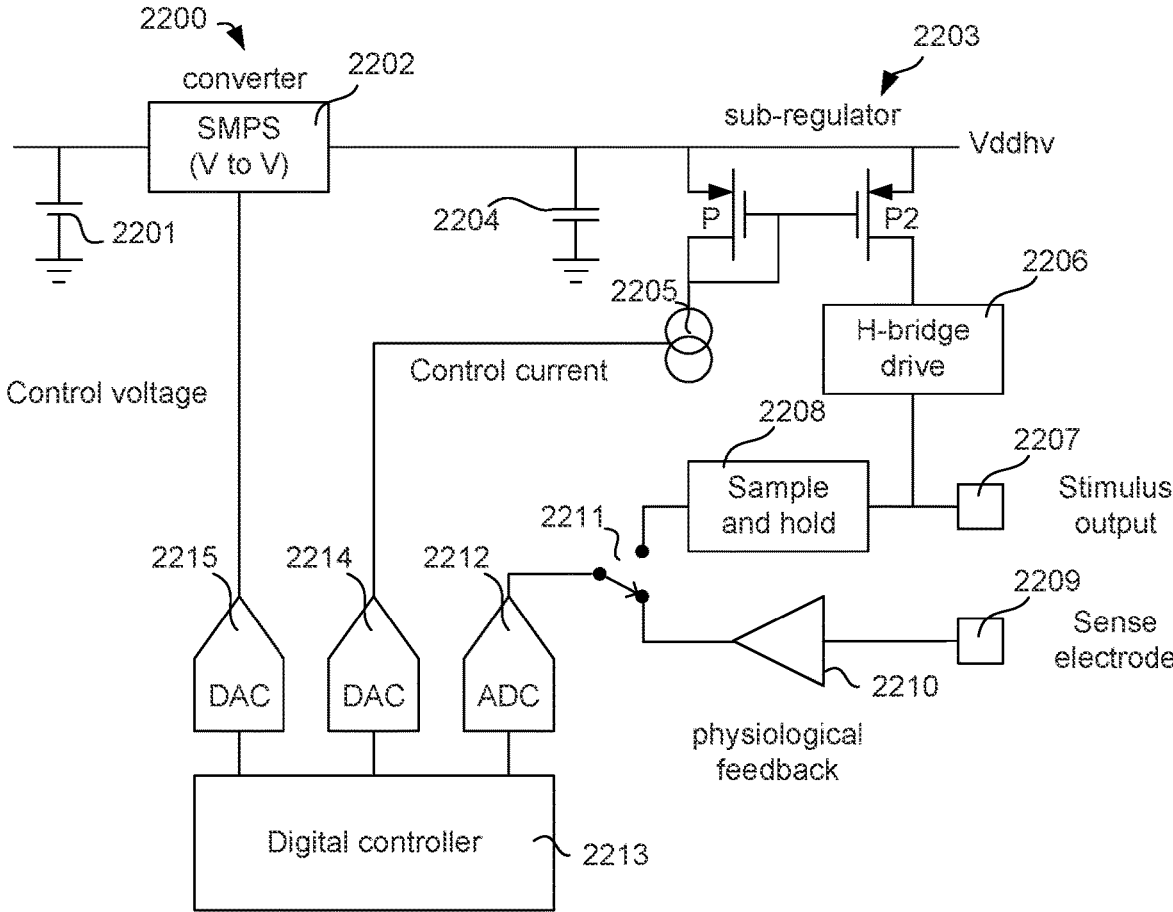
Fig. 22

2300

2400

2500

2501 generating a stimulation voltage signal at a stimulation voltage

2502 applying the stimulation voltage signal to neural tissue

2503 measuring a nervous response of the tissue

2504 adjusting the stimulation voltage based on the measured nervous response

POWER EFFICIENT STIMULATORS

CROSS-REFERENCE TO RELATED APPLICATIONS

The current application is a continuation of U.S. Non-Provisional patent application Ser. No. 16/969,886, filed Aug. 13, 2020, which is a U.S. National Stage Application of PCT Application Serial No. PCT/AU2019/050116, filed Feb. 15, 2019, which claims priority to Australian Patent Application Serial No. 2018900480, filed Feb. 15, 2018. The disclosures of U.S. Non-Provisional patent application Ser. No. 16/969,886, PCT Application Serial No. PCT/AU2019/050116 and Australian Patent Application Serial No. 2018900480 are hereby incorporated herein by reference in their entirety.

TECHNICAL FIELD

This disclosure relates to devices for applying a neural stimulus.

BACKGROUND

Neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord or dorsal root ganglion (DRG).

Such a system typically comprises an implanted electrical pulse generator and a power source, such as a battery, that may be rechargeable by transcutaneous inductive transfer. An electrode array is connected to the pulse generator and is positioned in the dorsal epidural space above the dorsal column. An electrical pulse applied to the dorsal column by an electrode causes the depolarisation of neurons and generation of propagating action potentials. The fibres being stimulated in this way inhibit the transmission of pain from that segment in the spinal cord to the brain.

While the clinical effect of spinal cord stimulation (SCS) is well established, the precise mechanisms involved are poorly understood. The DC is the target of the electrical stimulation as it contains the afferent A-beta fibres of interest. A-beta fibres mediate sensations of touch, vibration and pressure from the skin. The prevailing view is that SCS stimulates only a small number of A-beta fibres in the DC. The pain relief mechanisms of SCS are thought to include evoked antidromic activity of A-beta fibres having an inhibitory effect and evoked orthodromic activity of A-beta fibres playing a role in pain suppression. It is also thought that SCS recruits A-beta nerve fibres primarily in the DC with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect.

Effects can be inhibitory e.g. used to modulate an undesired process such as the transmission of pain, or stimulatory e.g. causing a desired effect such as the contraction of a muscle.

Spinal cord stimulators provide tissue stimulation using electrodes and circuits to deliver electrical energy to the nervous tissue. They can use charge balanced biphasic pulses or monophasic pulses with resistors and capacitors for charge recovery. Some stimulators use tri-phasic stimulation.

FIG. 1 illustrates a spinal cord stimulator using an example power path. A battery 101, typically 3.25-4.2V provides power to a switch-mode power supply 102 that pumps the voltage to a supply called VddHV, at typically 8-15V. A current mirror (P1, P2) 103 controlled by a reference current 104 creates a controlled current which then flows through switches 105, 106, 107, 108 to tissue 109. The switches 105, 106, 107, 108 are arranged in an H-bridge allowing current to be driven using either polarity into the tissue. With the switches 105, 106, 107, 108 in the position shown, charge flows from left to right. A shorting switch allows unbalanced charge to be recovered. Alternately this can be achieved by closing switch 107 and switch 108 together. Capacitors 110 and 111 block DC current from flowing in tissue 109. By using two such capacitors, no DC current can flow even when one capacitor fails. The voltage across the tissue 109 can be as high as 14V, so VddHV values of 16.5V are common.

It takes power to drive current into tissue. This power is drawn from the battery 101 and drains it so that it must be recharged regularly. Recharging the battery is an inconvenience to the patient. It is desirable to build a stimulator that is as efficient as possible, while not changing stimulation strength as the patient changes posture.

With current drive, the battery is pumped up to VddHV which exceeds the maximum induced tissue voltage by at least 0.5V, which is used to bias the current driver transistors. This 'lost' voltage is marked as $V_{loss}$ 112 and can be expressed as Vloss=VddHV−Vload and Ploss=Iload (VddHV−Vload). Power is dissipated in the implant when the current flows through the transistors of current source 103.

The power lost can also be given by the following equation where $V_L$ is the lost voltage and I is the stimulation current.

$$P = V_L I$$

Since a single value of VddHV is often chosen, when the patient has the stimulation strength turned low, the power lost in the drive transistors can exceed the power delivered to the patient. It is clearly desirable to reduce this lost power to maximize battery life and so improve patient convenience. In general, switched-mode power supplies obey conservation of power, with the current and voltage on input and output being related (ignoring the switcher efficiency term) by:

$$P = V_{DDHV} I_{PATIENT} = V_{BATTERY} I_{BATTERY}$$

It is thus recognized that if $V_{DDHV}$ is pumped to 16V, for example, but the patient tissue only requires 4V, 75% of energy drawn from the battery is wasted. If the rest of the implant were to be designed to use less power than this (as is desirable) then the time between battery recharges is potentially 4 times shorter than it need be.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A device for applying a neural stimulus comprises:

a battery to supply electrical energy at a battery voltage;

an electrode to apply the electrical energy to neural tissue;

a circuit to measure the nervous response of the tissue; and a voltage converter to receive the electrical energy from the battery and to control a voltage applied to the electrode based on the measured nervous response of the tissue.

It is an advantage that the voltage converter controls the voltage applied to the electrode. In contrast to current control this direct voltage control is more energy efficient because losses across a typical current mirror is avoided. A further advantage is that the control based on the measured nervous response leads to automatic compensation of impedance variation due to in-growth or change in posture. As a result, the stimulation results in a desired neural response, which previously required current control with the associated low energy efficiency.

The converter may comprise a processor programmed to calculate a voltage value based on the measured nervous response and to generate a control signal to the voltage converter indicative of the calculated voltage value.

The converter circuit may be a linear voltage-to-voltage converter.

The converter may be a switched-mode voltage to voltage converter.

The converter may comprises a pulse generator configured to generate a pulse signal to control switching of the switched-mode voltage to voltage converter.

The pulse signal may be based on the measured nervous response of the tissue.

The pulse generator may be a digital processor.

The device may comprise an analog-to-digital converter to provide a digital signal indicative of the measured nervous response of the tissue to the digital processor.

The voltage to voltage converter may comprise a switch that is controlled by a control signal based on the measured nervous response of the tissue to thereby control the voltage applied to the electrode based on measured nervous response of the tissue.

The control signal may define a duty cycle based on the nervous response of the tissue, such that the control signal controls the switch and the duty cycle defines the output voltage to thereby control the voltage applied to the electrode based on the measured nervous response of the tissue.

The control signal may be an analog voltage signal provided by the processor and the voltage signal controls the switching of the switch to thereby control the voltage applied to the electrode based on the measured nervous response of the tissue.

The controller may comprise an oscillator with an oscillation frequency and the voltage signal controls the oscillation frequency to thereby control the voltage applied to the electrode based on the measured nervous response of the tissue.

A method for neural stimulation comprises repeatedly performing the steps of.

generating a stimulation voltage signal at a stimulation voltage;

applying the stimulation voltage signal to neural tissue;

measuring a nervous response of the tissue; and adjusting the stimulation voltage based on the measured nervous response.

Generating the stimulation voltage may comprises repeatedly switching a switched mode power supply; and adjusting the stimulation voltage may comprise adjusting a pulse signal that controls the switching.

A device for applying a neural stimulus comprises:

a battery to supply electrical energy at a battery voltage;

an electrode to apply the electrical energy to neural tissue;

a circuit to measure the nervous response of the tissue;

a current mirror to deliver a current to the electrode according to a reference current that is based on the measured nervous response; and a voltage converter to receive the electrical energy from the battery and to control a voltage applied to the current mirror based on a voltage between the stimulating electrodes.

It is an advantage that the voltage converter controls the voltage applied to the current mirror based on the voltage between the electrodes. This means the voltage applied to the current mirror can be reduced to reduce the voltage drop across the current mirror and thereby reduce the power dissipated in the current mirror.

The converter may be a switched-mode voltage converter.

A device for applying a neural stimulus comprises:

a battery to supply electrical energy at a battery voltage;

an electrode to apply the electrical energy to neural tissue;

a circuit to measure the nervous response of the tissue;

a switched mode voltage to current converter to receive the electrical energy from the battery and to control a current applied to the stimulating electrode; and a controller to control switching of the switched mode voltage converter based on the measured nervous response of the tissue.

The controller may control the switching based on the battery voltage.

The controller may control the switching based on an electrode voltage

The controller may control the switching based on a desired stimulation intensity.

The controller may comprise a pulse generator to generate a pulse signal to control the switching.

The controller may comprise a voltage controlled oscillator to generate the pulse signal.

The controller may comprise a voltage controlled delay controlled by the battery voltage to control the switch.

The voltage controlled delay may be connected to a switch to disconnect an inductance from the battery after a delay controlled by the battery voltage.

The voltage controlled delay may be connected to the switch to disconnect the inductance from the battery after a delay controlled by a tissue voltage.

The voltage controlled delay may be connected to the switch to disconnect the inductance from the battery after a delay controlled by a desired level of stimulation intensity.

The controller may comprise a voltage controlled oscillator to control a frequency of the pulse signal based on a desired level of stimulation and tissue voltage and a voltage controlled delay to control a time period for which the switch connects the inductance to the battery at each oscillation based on the battery voltage.

The pulse signal may be periodic and controlling the switch comprises suppressing pulses that turn the switch on to set the amount of energy provided by the inductance.

A device for applying a neural stimulus comprises:

a battery to supply electrical energy at a battery voltage;

an electrode to apply the electrical energy to neural tissue;

a circuit to measure a nervous response of the neural tissue;

a pulse generator to generate stimulation current pulses at a pulse length and to adjust the pulse length based on the measured nervous response of the neural tissue.

The circuit to measure the nervous response of the neural tissue may comprise a template signal and the circuit is configured to shift the template signal in time relative to the stimulation current pulses based on the pulse width.

The circuit may comprise a look-up table storing delay values for the template signal for each of multiple pulse width values.

BRIEF DESCRIPTION OF DRAWINGS

FIG. 1 illustrates a spinal cord stimulator using an example power path.

An example will now be described with reference to the following drawings:

FIG. 2a illustrates the resulting voltage and current waveforms for voltage stimulation.

FIG. 2b illustrates the voltage and current waveforms for current stimulation.

Figure 3:
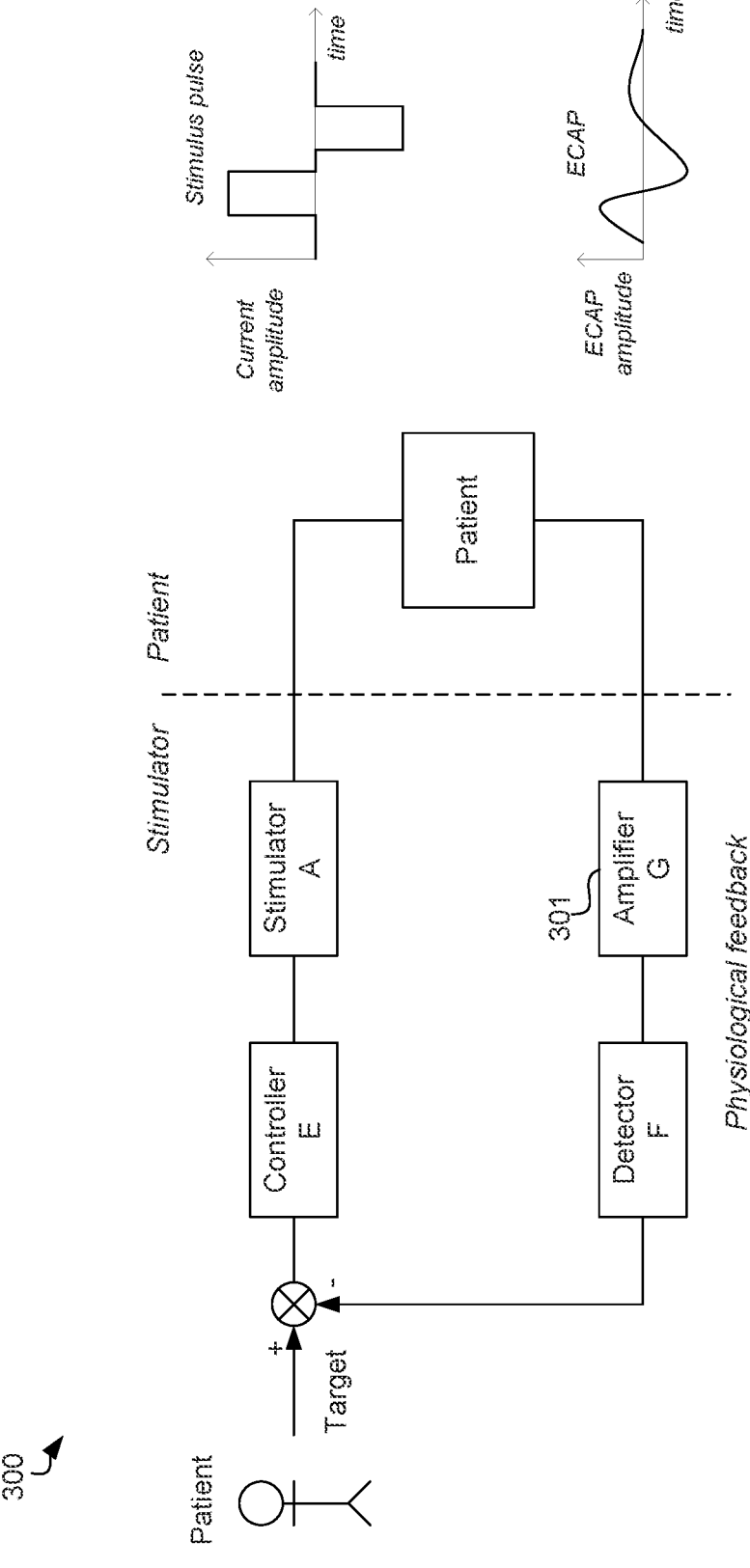

FIG. 3 shows a general architecture 300 of a stimulator with feedback.

Figure 4:
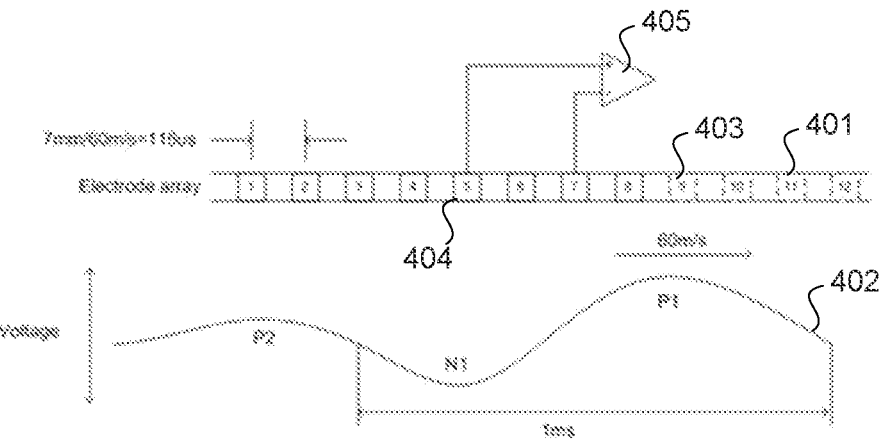

FIG. 4 illustrates an example array of electrodes.

Figure 5:
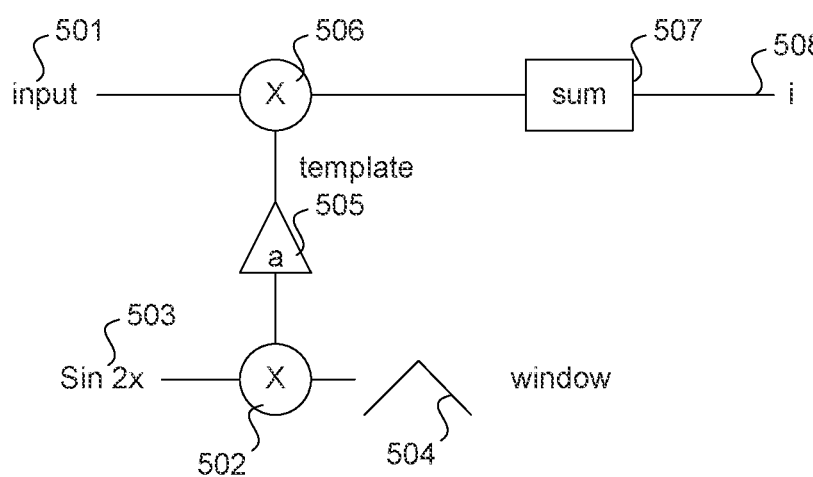

FIG. 5 illustrates a signal flow for processing the output signal from amplifier 405 in FIG. 4.

Figure 6A:
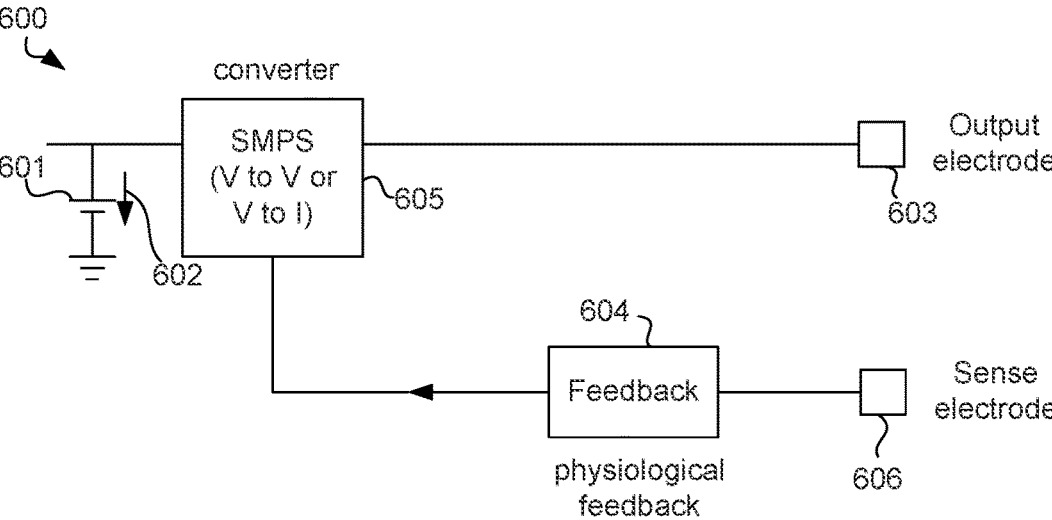

FIG. 6a illustrates an example device for applying a neural stimulus.

Figure 6B:
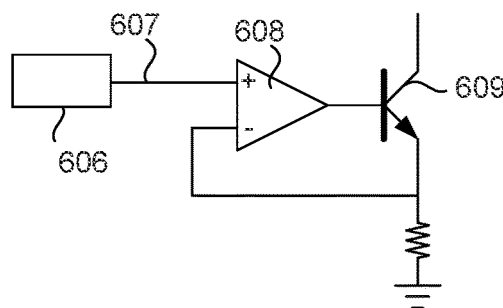

FIG. 6b illustrates an example linear voltage-to-current controller.

Figure 7:
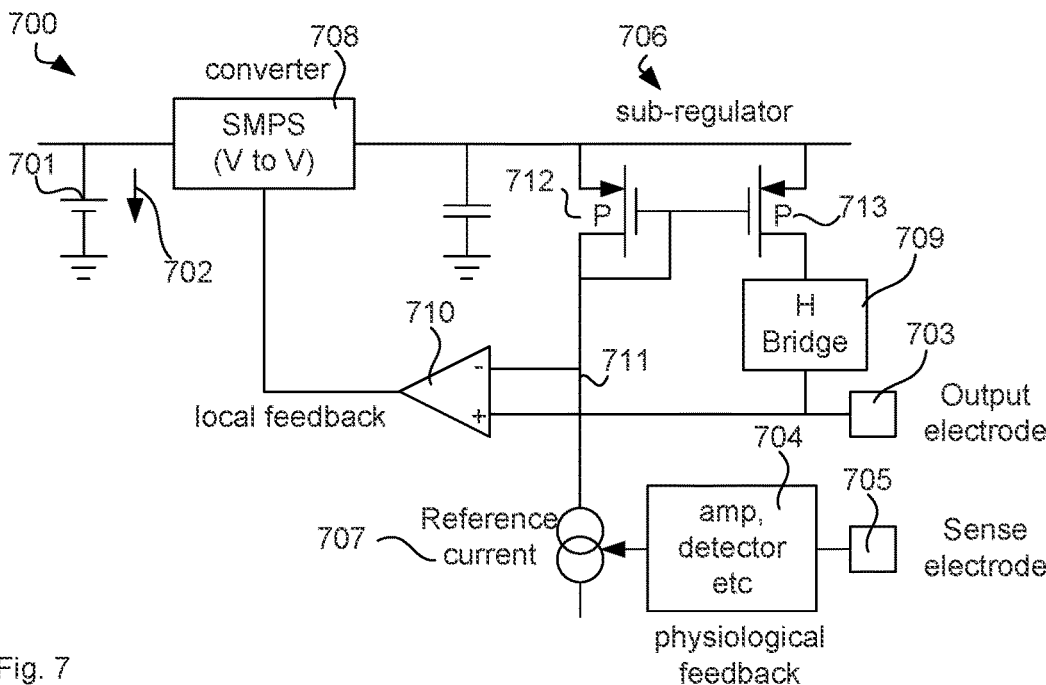

FIG. 7 illustrates another example device for applying a neural stimulus.

FIG. 8 illustrates a variation of the device in FIG. 7 where an additional transistor is included.

FIG. 9 illustrates a further example device for applying a neural stimulus.

Figure 10:
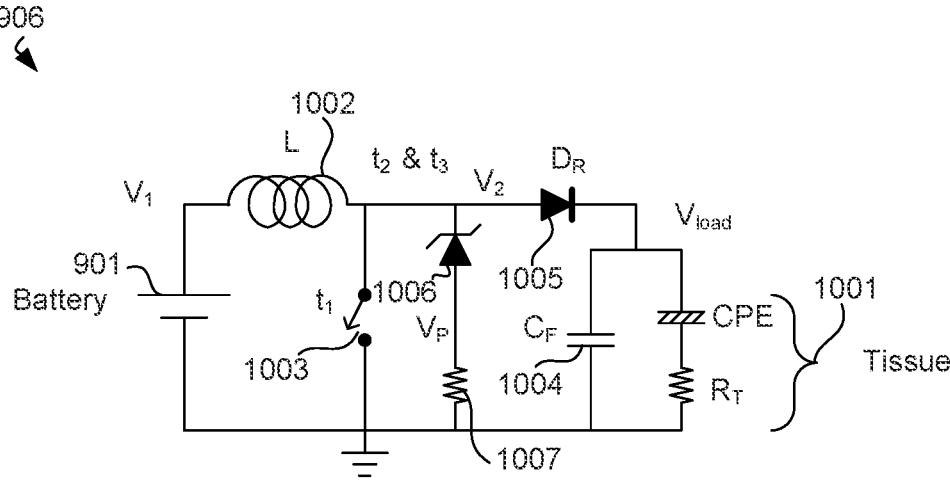

FIG. 10 illustrates converter 906 from FIG. 9 in more detail.

Figure 11:
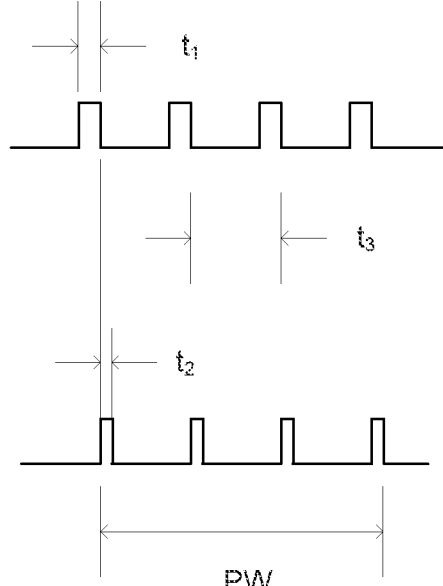

FIG. 11 illustrates the operation switch 1003 from FIG. 10 in the context of neural stimulation.

Figure 12:
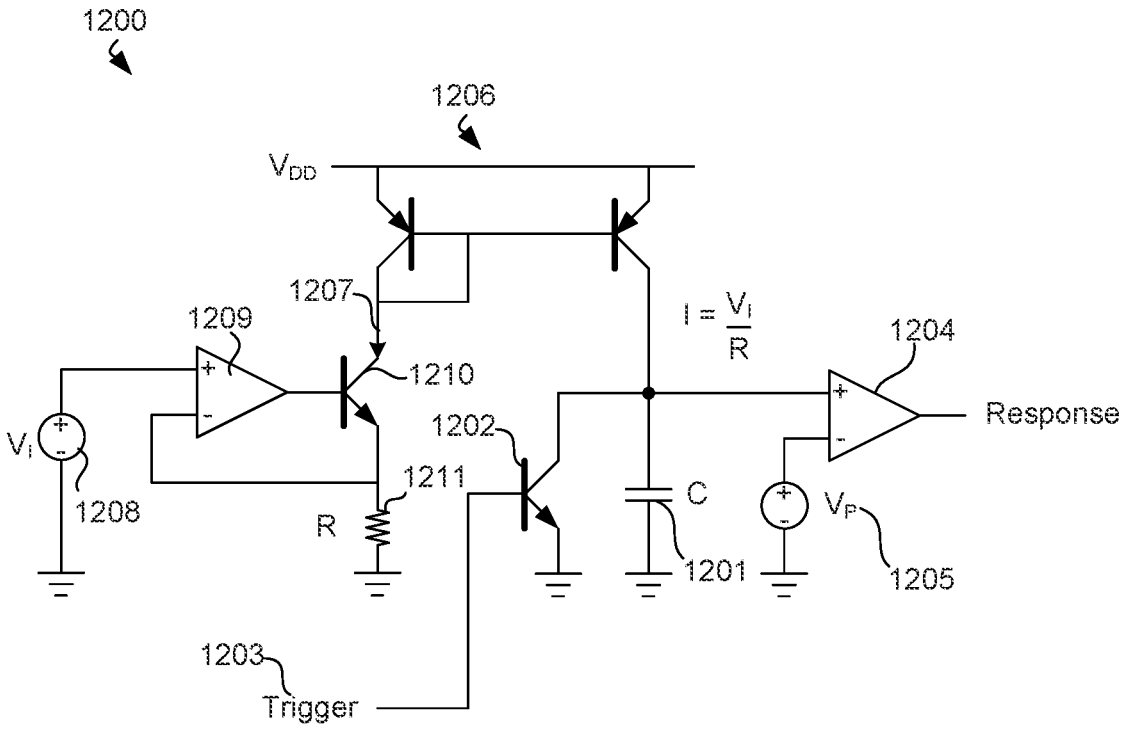

FIG. 12 illustrates a time delay circuit.

Figure 13:
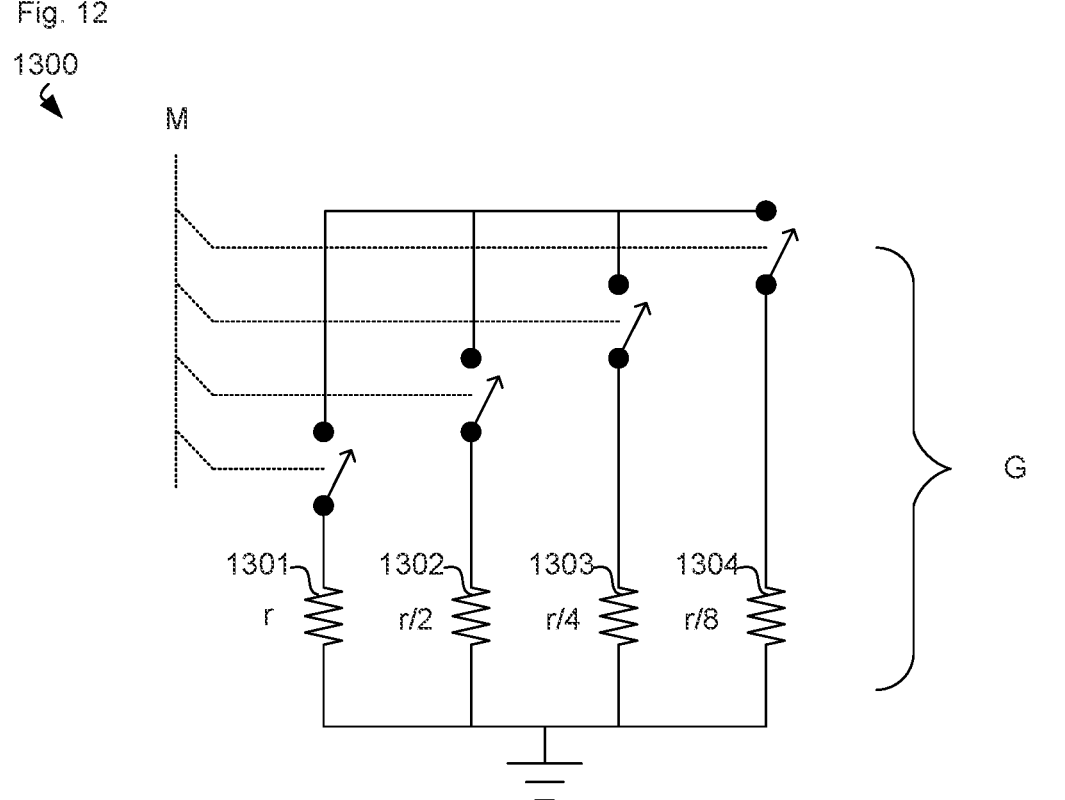

FIG. 13 illustrates a digital controlled resistor circuit.

Figure 14:
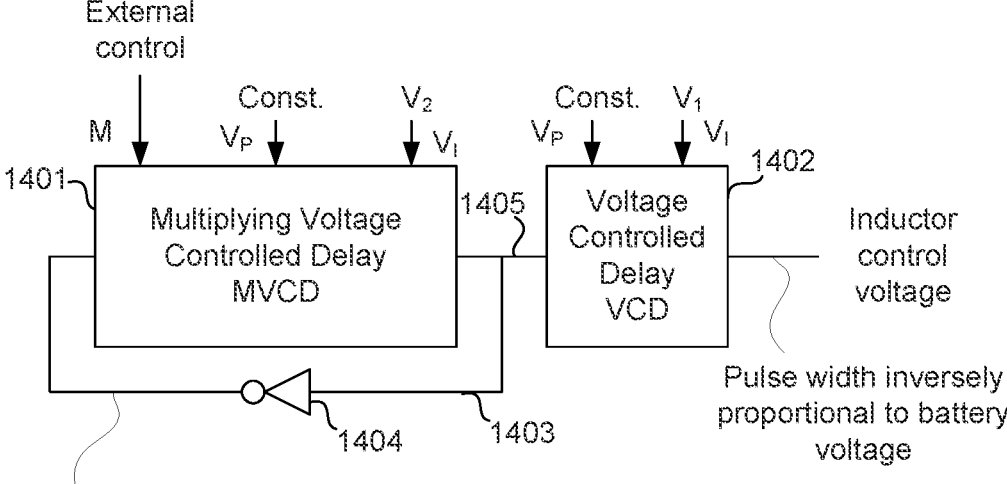

FIG. 14 illustrates a control circuit 1400 which implements the feedback circuit 904 in FIG. 9.

Figure 15:
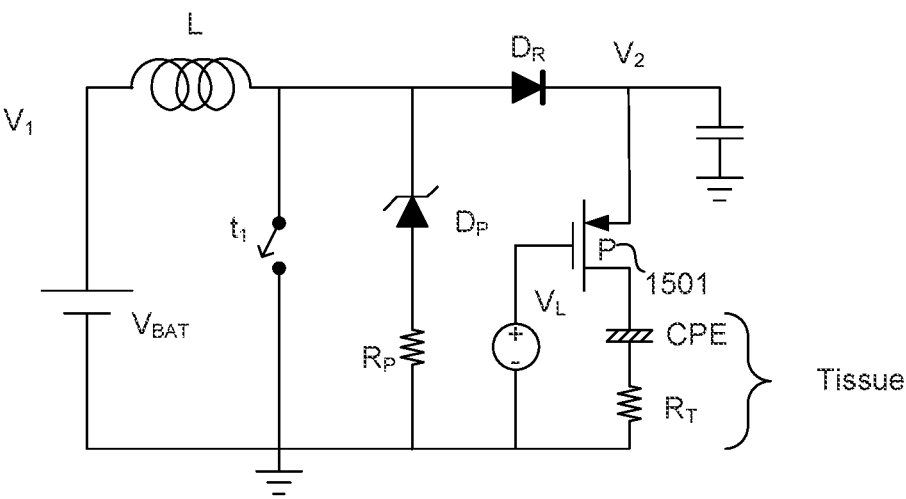

FIG. 15 illustrates a switched mode voltage converter with cascode p-channel FET in the output path.

Figure 16:
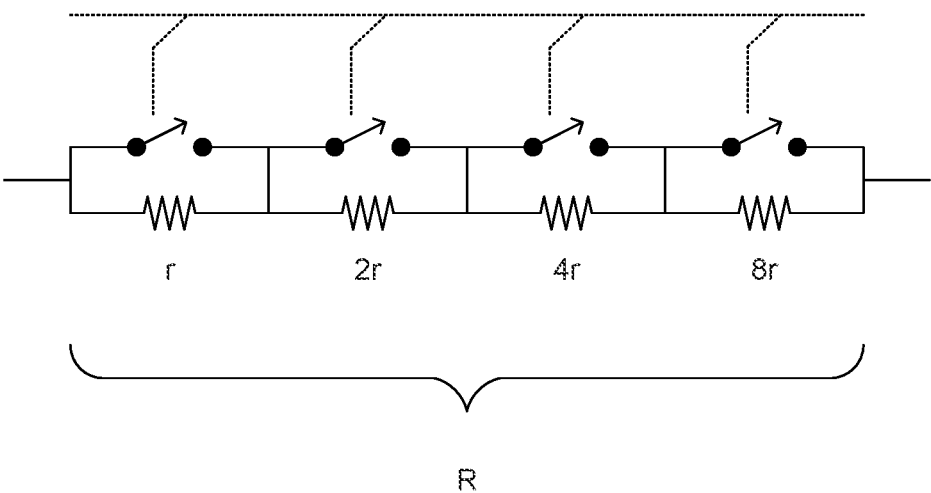
Figure 17:
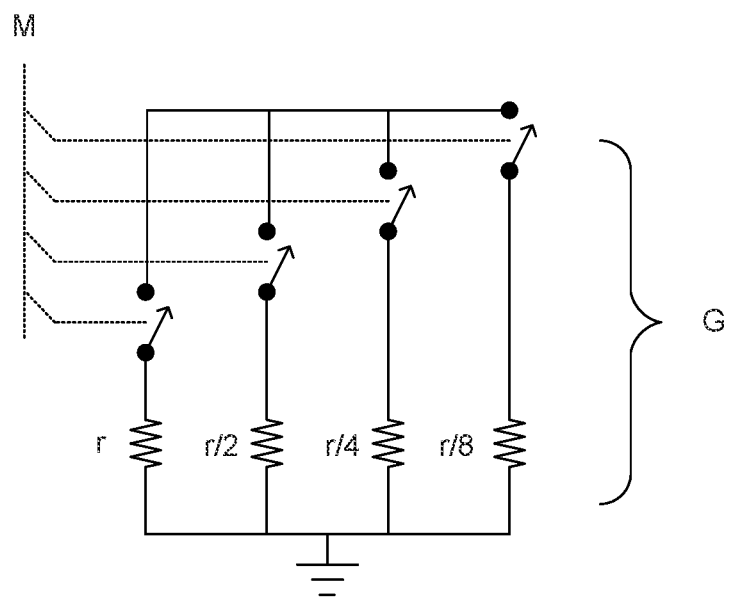

FIGS. 16 and 17 show examples of a digitally controlled resistance or conductance, respectively.

Figure 18:
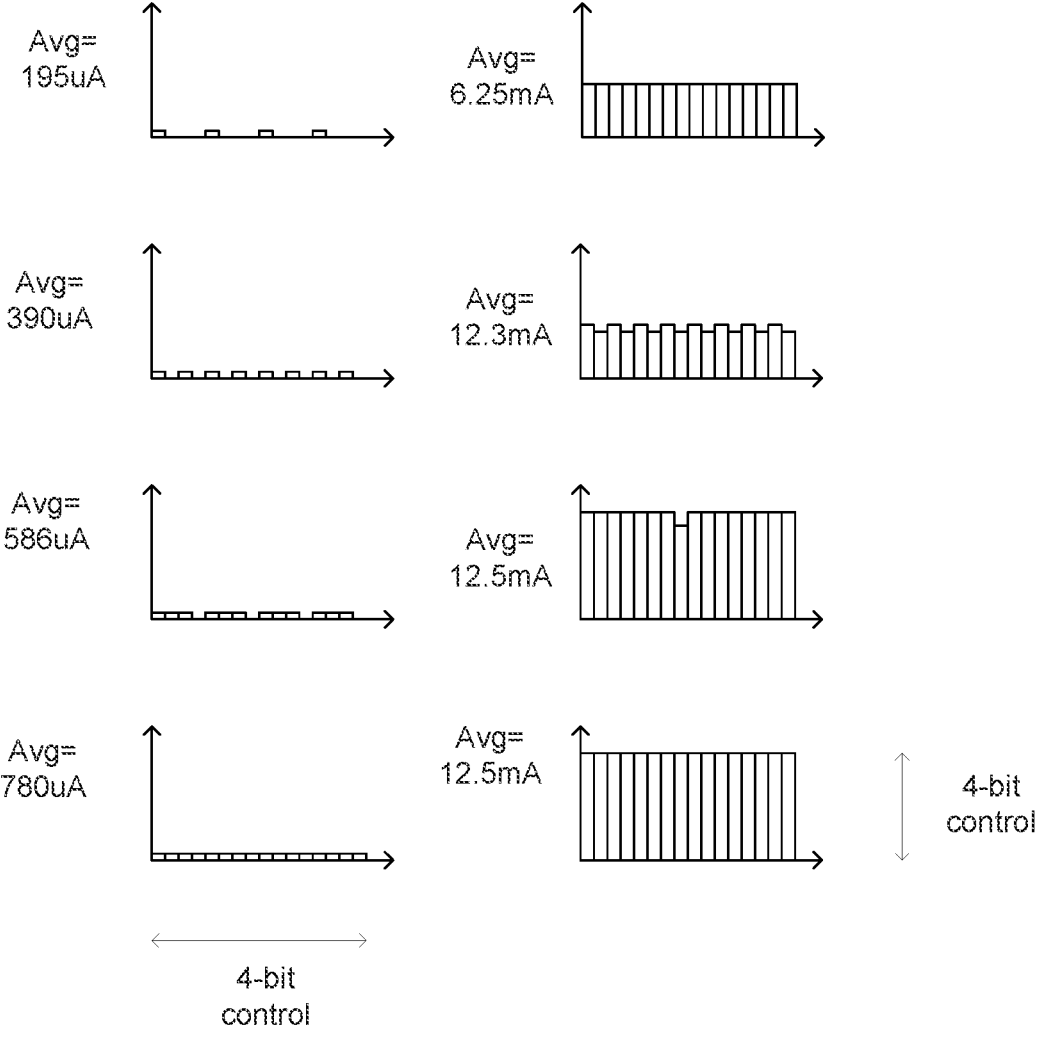

FIG. 18 illustrates a deterministic way of combining two amplitude controls in a pulse modulation system.

Figure 19:
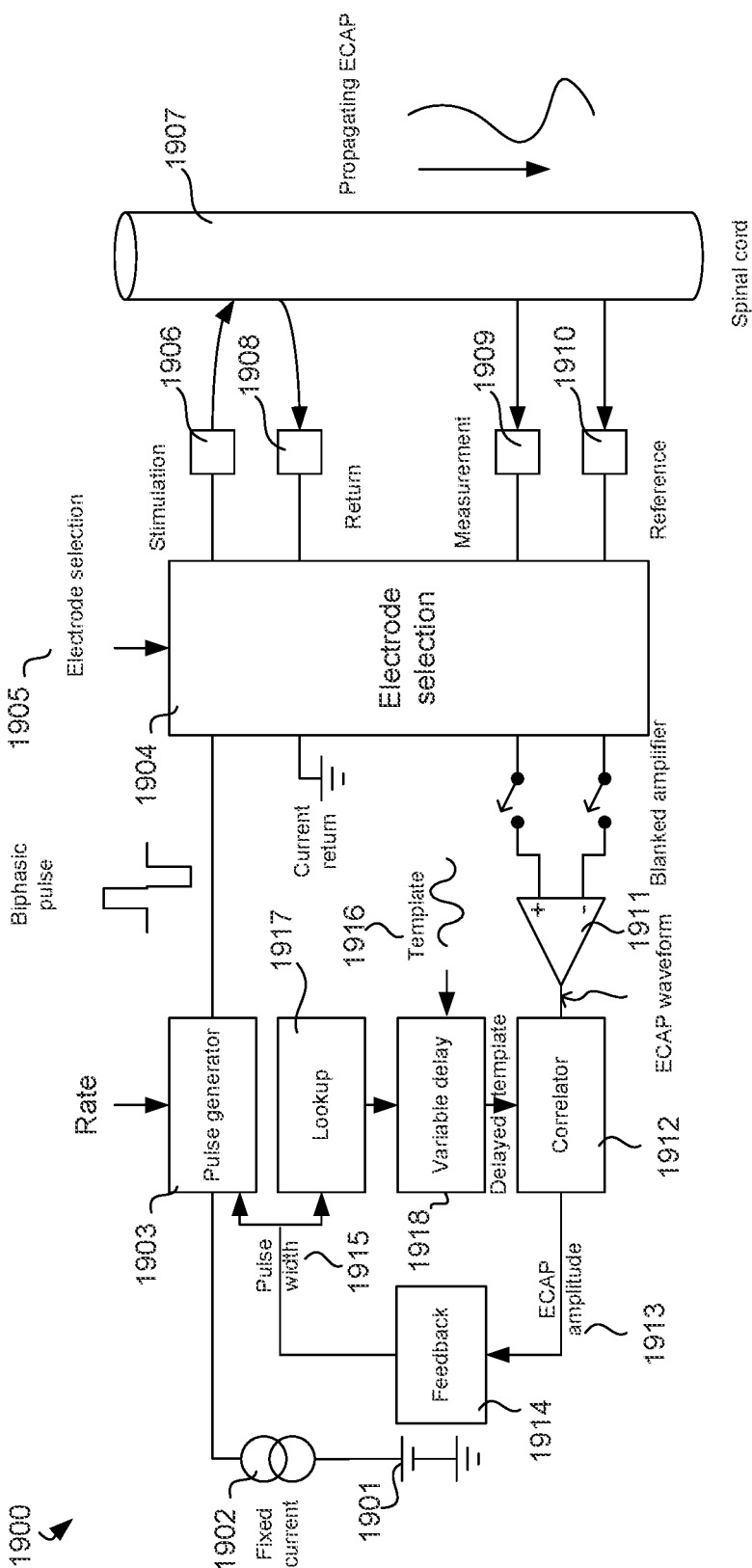

FIG. 19 illustrates another example for a device 1900 for applying a neural stimulus.

Figure 20:
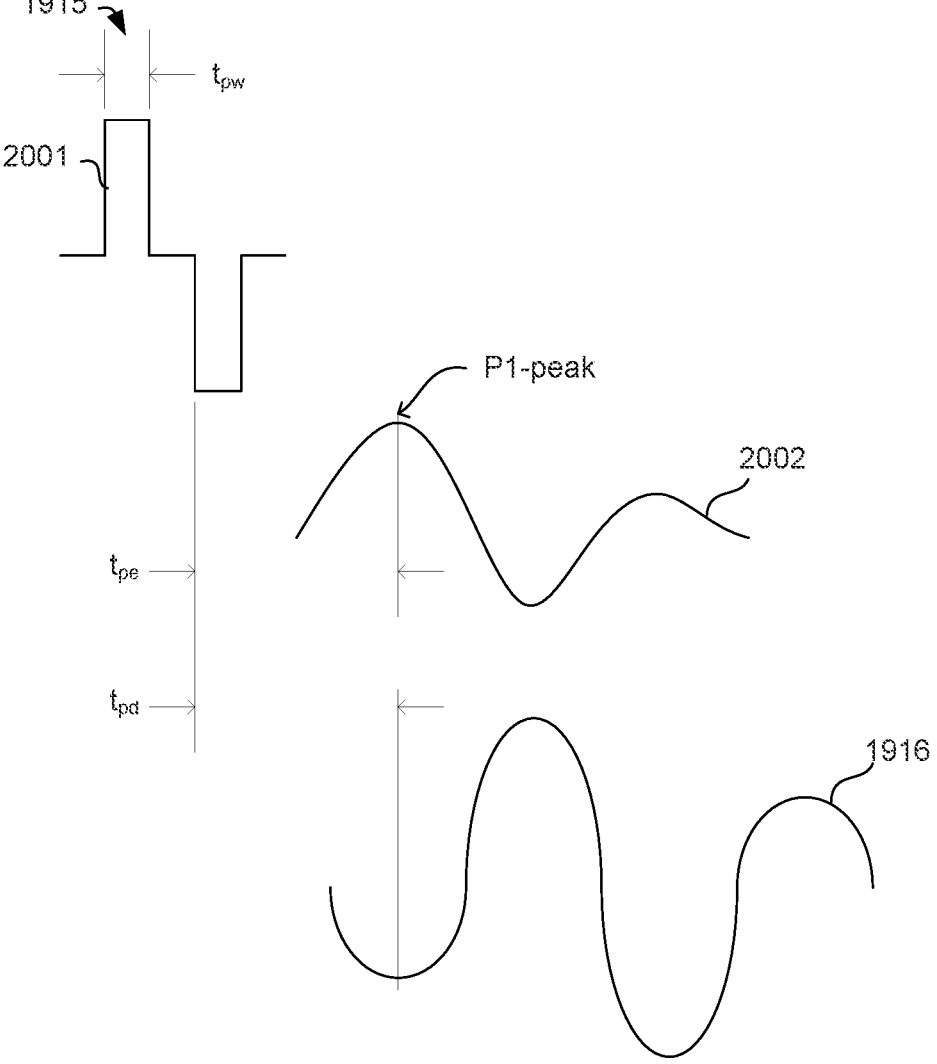

FIG. 20 illustrates a stimulus and the alignment between ECAP and template.

FIG. 21 illustrates a further example where the feedback control is implemented directly in the converter.

FIG. 22 illustrates a further example stimulation device.

Figure 23:
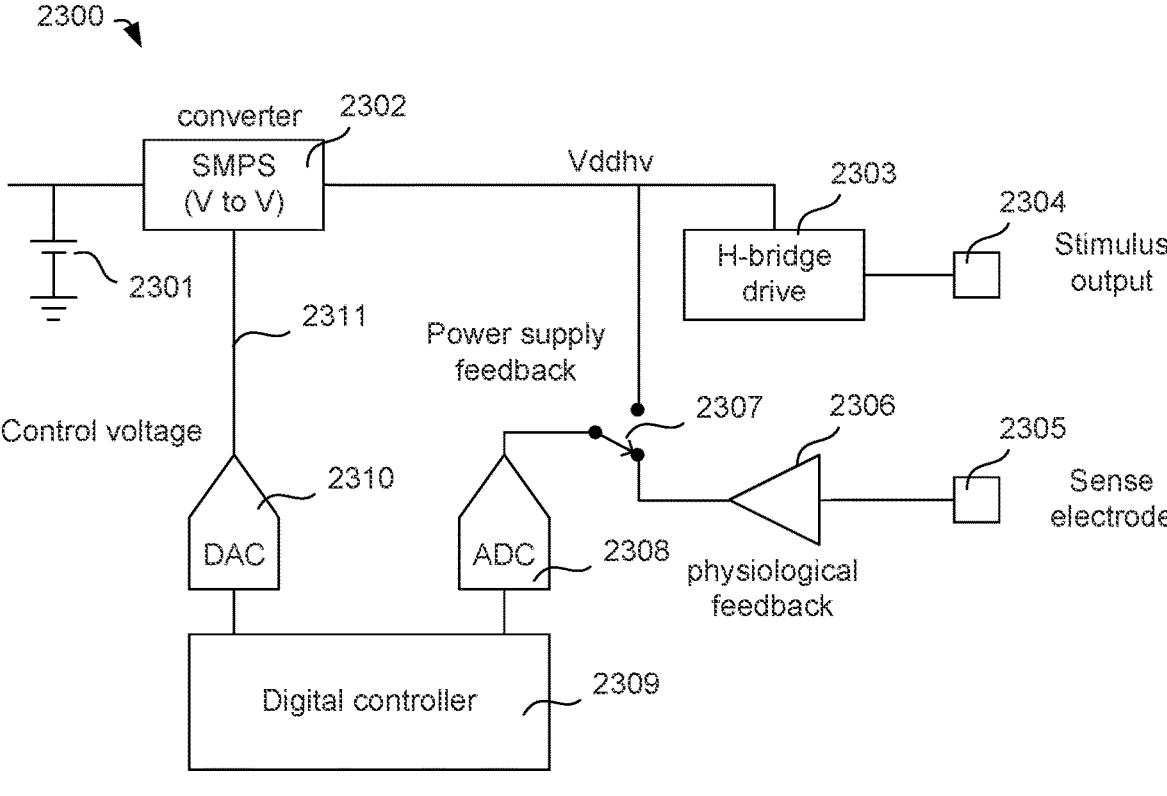

FIG. 23 illustrates a voltage-drive version of FIG. 22.

Figure 24:
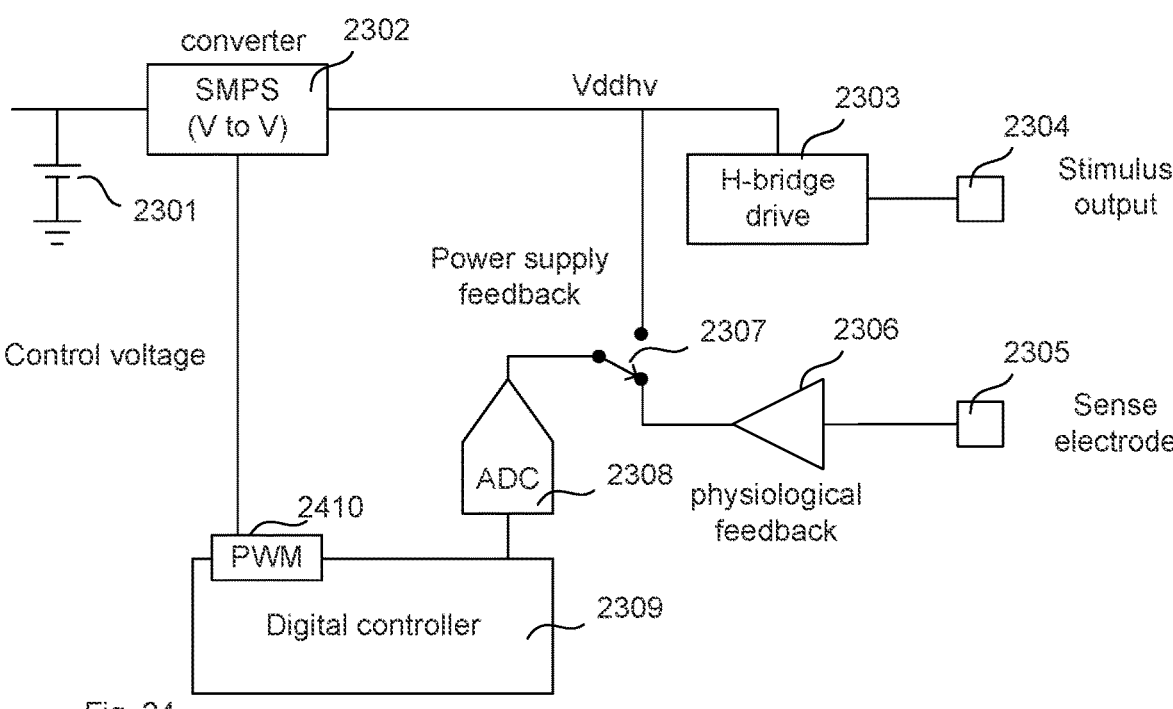

FIG. 24 illustrates a further implementation of an implantable stimulation device where, compared to FIG. 23, the DAC is omitted and the controller directly provides the timed pulses for the switching in switched-mode power supply converter.

Figure 25:
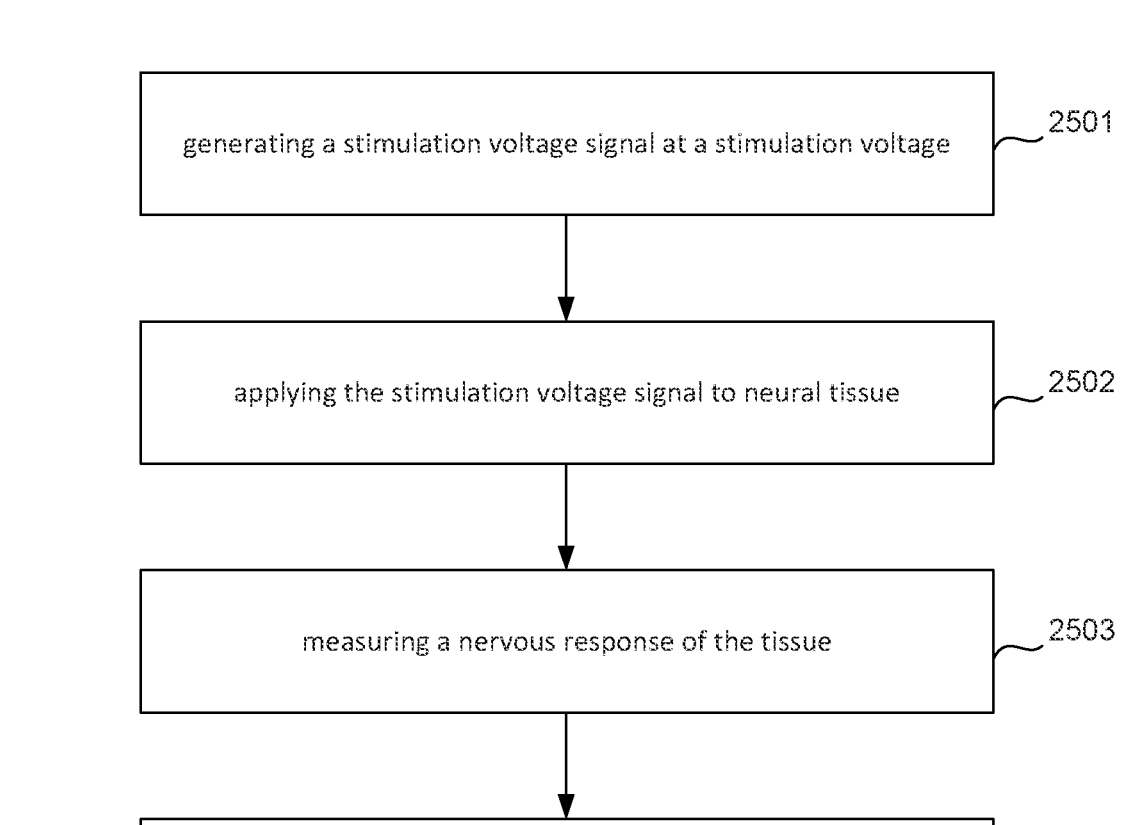

FIG. 25 illustrates a method for neural stimulation.

DESCRIPTION OF EMBODIMENTS

In many cases current drive is preferred by patients as they find wide pulse widths more 'soothing'. Due to the reactive nature of the tissue electrode interface, when tissue is driven with a voltage source, the current has a large spike at the beginning, then tails off. FIG. 2a illustrates the resulting voltage and current waveforms for voltage stimulation. FIG. 2b on the other side, illustrates the voltage and current waveforms for current stimulation. The voltage stimulation is akin to a narrow stimulation pulse. In contrast, with current drive, a wide rectangular stimulation can be produced which is preferred.

This disclosure will focus on systems using biphasic stimulation, although methods described can be adapted to greater or lesser numbers of phases. It will also describe both voltage and current source systems.

FIG. 3 shows a general architecture 300 of a stimulator. An amplifier 301 amplifies a physiological signal that, for an evoked compound action potential (ECAP), will typically be 10 uV to 100 uV. Its amplitude is then detected using a variety of methods, though a correlator and 4-lobe detector is preferred. FIG. 4 illustrates an example array of electrodes 401, which are spaced apart by 7 mm. At a typical propagation velocity of the ECAP of 60 m/s, the travel time between two adjacent electrodes is 116 μs. FIG. 4 also shows the ECAP waveform 402 at the same scale as the electrode array 401 to illustrate the wavelength against the size of the electrode. At the currently illustrated point in time, the ninth electrode 403 measures the P1 peak of the ECAP and the fifth electrode 404 measures the N1 peak. A differential amplifier 405 amplifies the difference between two electrodes which results in a filter for the ECAP signal. The distance between two electrodes that are connected to the differential amplifier 405 may be between 14 mm and 42 mm, which relates to between 2 and 6 electrodes for a 7 mm spacing between adjacent electrodes.

FIG. 5 illustrates a signal flow for processing the output signal from amplifier 405 in FIG. 4, which is now input signal 501. A first mixer 502 mixes a reference sine wave 503 with a window function 504 and a gain module 505 scales the result by a weighting factor. A second mixer 506 mixes the scaled result with the input signal 501. A summation module 507 sums up the samples over the time window of the window function 504 similar to a continuous integral and provides an output signal 508. As a result of the mixing, the summed output reflects the similarity between the input signal and the windowed sine function, which is also referred to as a template function. That is, when the P1 peak of the ECAP signal coincides with the maximum of the sine function, the output 508 has a maximum value. When the input signal 501 is misaligned or contains mainly noise, the output 508 is minimal. One example of this correlation process is a four-lobe correlation where the length of the window function 504 spans four extrema of the sine wave, that is, the length of the window function 504 is twice the period of reference sine wave 503.

The described process is similar to a correlation function between two signals where one signal is time-shifted and integrated for each value of the correlation function. For this reason, the described process is also referred to as a correlation process and suppresses noise and artefacts such that the maximum of the correlation signal 508 can be used as a feedback value in the controls disclosed herein. The template can be time-aligned with the expected ECAP curve by calculating an expected time of arrival, which depends on the distance from the stimulating electrode assuming t=0 from the start of the cathodic (negative) pulse, where the ECAP begins to propagate. For example, it takes 467 us for the ECAP to travel to an electrode 28 mm from the stimulation site and PW is 120 us, then the sample delay is: 467–PW=347 us. Time of arrival can also be simply measured. Further details of ECAP measurement are provided in WO 2014/071445 and WO 2014/071446, which are both included herein by reference.

Once the evoked response amplitude has been calculated, such as the value of the correlation, a comparator compares the amplitude of the detected evoked response with the desired response. A controller integrates the error signal at a rate that sets the loop time constant and a stimulator then generates a controlled stimulus pulse. Either the amplitude or the pulse width may be controlled.

Voltage Drive with Feedback

FIG. 6a illustrates an example device 600 for applying a neural stimulus as described above. The device 600 comprises a battery 601 to supply electrical energy at a battery voltage 602 and an electrode 603 that applies the electrical energy to neural tissue (not shown). Device 600 further comprises a circuit 604 that measures the nervous response of the tissue, such as the ECAP described above. Further, there is a voltage converter 605 that receives the electrical energy from the battery and controls a voltage applied to the electrode based on the nervous response of the tissue measured by circuit 604. As shown in FIG. 6 the ECAP may be measured by a sense electrode 606, which may be located at a distance from the stimulation electrode 603 as described above with reference to FIG. 4. This way the sense electrode 606 can capture the evoked neural response once it has travelled the distance between the output electrode 603 and the sense electrode 606. To avoid error measurements, the ECAP detection is disabled during the stimulation itself and shortly thereafter. This reduces artefacts caused by the settling of the circuitry, such as operational amplifiers.

It is noted that when the stimulator 600 in FIG. 6a is compared to prior art stimulator 100 in FIG. 1, the voltage converter 605 is connected directly to the output electrode 603 without the use of a current driving circuit, such as current mirror 103. The power-saving stimulator design presented in FIG. 6 combines voltage drive and local feedback. The feedback compensates for the changes in stimulation current with tissue growth and posture. As the tissue is driven directly, the power that is dissipated by current mirror 103 (as shown in FIG. 1) is saved, which means the battery 601 lasts longer without being re-charged. At the same time, the feedback 604 of the evoked response allows the control of the output voltage such that a desired response can be maintained, which would previously have been achieved by current mirror 103 without feedback.

In one example, the converter 605 comprises digital circuitry, such as a microprocessor, in contrast to analogue circuitry, such as operational amplifiers and current mirrors. In the digital case, the microprocessor calculates a voltage value that is to be applied to the electrode 603. The voltage value may be in the form of an binary number, such as an 8 bit string. An digital to analogue converter can then convert the bit string into a voltage and delivered to electrode 603 through a driver circuit. The processor may have stored on memory a desired value of neural stimulation, which can be adjusted externally by the patient or the clinician. In that case, the processor receives the measured ECAP from circuit 604 and compares the received ECAP with the stored desired ECAP. If the received ECAP is less than the desired ECAP, the processor increases the voltage. On the other hand, if the received ECAP is greater than the desired ECAP, the processor decreases the voltage. The processor may also implement a proportional/integral/differential (PID) control mechanism which optimally responds to changes in the ECAP. The input (process variable) of the PID control is the measured ECAP while the error value is the difference of the input to the stored desired ECAP and the output is the electrode voltage or an output signal that directly controls the electrode voltage. This can be useful if the patient moves and the impedance of the electrodes changes or more generally the evoked response changes for a given electrode voltage. The PID control loop can be parameterised for different objectives, such as fast response or minimal overshoot to avoid patient discomfort. The general PID calculation is given by $$u(t) = K_p e(t) + K_i \int_0^t e(t)dt + K_d \frac{de(t)}{dt}.$$

In another example, the voltage converter 605 comprises a linear voltage-to-voltage converter also referred to as linear voltage regulator. In such a case, the processor provides an output signal to the linear voltage-to-voltage converter to control the linear voltage-to-voltage converter to adjust the voltage as indicated by the PID control method. FIG. 6b illustrates an example where processor 606 provides a control signal 607 to an operational amplifier 608 that drives the gate of an output transistor 609. This means the output voltage of the processor 606 or DAC connected to the processor 606 constitutes the output value of the PID control. It is noted that the linearity of the regulator, such as the output transistor 609, is not crucially important because the PID control automatically adjusts the voltage by relatively small variations and a slight non-linearity should not affect the operation of the overall control loop.

In yet another example, the voltage converter 605 in FIG. 6a comprises a switched-mode voltage to voltage converter. In this case, the processor controls the duty cycle of the switching, that is, the processor varies the ratio of on-to-off time. During the on-time an inductor is charged while during off-time the energy stored in the inductor is consumed by the electrodes. According to the principle of switched-mode voltage converters, a higher duty cycle increases the output voltage while a lower duty cycle reduces the output voltage. Consequently, the processor can control the output voltage by controlling the duty cycle.

Current Drive with Local Feedback

FIG. 7 illustrates another example device 700 for applying a neural stimulus. Device 700 comprises a battery 701 to supply electrical energy at a battery voltage 702 and an electrode 703 to apply the electrical energy to neural tissue. A circuit 704 connected to a sense electrode 705 measures the nervous response of the tissue. In this case, the device performs current drive and therefore comprises a current mirror 706 to deliver a current to the electrode 703. A reference current source 707 provides a constant reference current to current mirror 706, which can be adjusted by the clinician or the patient to adjust the level of perceived effect of the stimulation. The reference current source 707 is also controlled by the neural response measured by circuit 704. Current mirror 706 then mirrors the reference current from source 707 and delivers it to the output electrode 703. As a result, the current delivered to the output electrode is based on the measured nervous response in the sense that a lower response leads to an increased reference current and a higher response leads to a lower reference current. Again, the circuit 704 may include a processor and the processor may perform PID control to generate the signal that controls the reference current source 707.

Importantly, a voltage converter 708 receives the electrical energy from the battery and controls a voltage applied to the current mirror based on a voltage between the stimulating electrodes. This means the voltage applied to the current mirror can be reduced to reduce the voltage drop across the current mirror and thereby reduce the power dissipated in the current mirror. There is also an H-Bridge 709 to switch the output current to the output electrode 703.

In the example of FIG. 7 device 700 comprises an operational amplifier 710 (i.e. differential amplifier) that provides the feedback signal to converter 708. The inputs of amplifier 710 are connected to the output electrode 703 and the drain 711 of a first transistor 712 of sub-regulator 706, which also comprises a second transistor 713. Since the gates of the first transistor 712 and the second transistor 713 are connected, the gate source voltage is identical leading to approximately identical drain currents according to the principles of current mirrors. The difference between the gate voltage and the electrode voltage is then the gate drain voltage of the second transistor 713. The aim should be to keep this voltage to a minimum to reduce the power dissipated in the second transistor 713. Therefore, the output of amplifier 710 is connected as a control input to voltage converter 708 such that the voltage converter 708 reduces its output voltage when there is a large gate drain voltage across the second transistor. In other words, if a large voltage is created on stimulation electrode 703, the gate-drain voltage across second transistor 713 will be low and converter 708 will keep or increase its output voltage. On the other hand, if a low voltage is created on stimulation electrode 703 (due to lower tissue impedance, for example) the gate drain voltage across second transistor 713 is larger, which causes converter 708 to decrease its output voltage thereby reducing losses across second transistor 713.

The $V_{loss}$ term is kept to one transistor turn-on voltage and power loss is reduced. The drain-source voltage of second transistor 713 is just sufficient for second transistor 713 to be saturated, where a simple mirror operates it with a drain voltage equal to the saturation voltage plus a threshold. For a typical CMOS process with threshold voltages of 0.5V, additional improvement can be obtained by biasing second transistor 713 closer to its saturation limit as shown in FIG. 8 where an additional transistor 801 is included between first transistor 712 and the reference current 707.

In one example, converter 708 is a switched-mode voltage converter where the duty cycle of charging the internal inductance depends on the output signal of amplifier 710.

FIG. 9 illustrates a further example device 900 for applying a neural stimulus. Device 900 comprises a battery 901 to supply electrical energy at a battery voltage 902. Device 900 further comprises an electrode 903 to apply the electrical energy to neural tissue and a circuit 904 connected to a sense electrode 905 to measure the nervous response of the tissue. There is also a switched mode voltage to current converter 906 to receive the electrical energy from battery 901 and to control a current applied to the stimulating electrode 903. Importantly, there is no current mirror in FIG. 9 because the switched mode converter 906 provides the current directly to output electrode 903. Circuit 904 is connected to converter 906 to control switching of the switched mode voltage converter based on the measured nervous response of the tissue. In other words, this takes the feedback control 904 directly into the converter 906, and avoids the use of a sub-regulator 706 in FIGS. 7 and 8. The solution described in FIG. 9 and the related subsequent Figures provide most of the benefits of voltage drive, while fitting within the framework of existing clinical systems. This means there is provided a way to build a current source for tissue stimulation that uses less power than previous implementations.

Current source stimulators typically provide current over a range from 50 uA to 12.5 mA and should be selectable. Device 900 provides a fixed pulse width that is stable from one stimulation cycle to the next. As a result, the ECAP appears at a predictable time and can be detected. The pulse width is usually adjusted by the clinician to a value that is preferable to a patient. The battery voltage changes as the battery is discharged and the tissue voltage changes during the stimulation pulse. The current mirror 103 in FIG. 1 addresses these issues but the problem of power loss remains.

FIG. 10 illustrates converter 906 in more detail, which comprises a charge pump to multiply the battery voltage 902 to the higher voltage used to stimulate the tissue. It is noted that the charge pump 906 is connected directly to tissue 1001. Importantly, converter 906 comprises an inductor 1002 and a switch 1003 that closes a circuit including only inductor 1002 and battery 901. As a result, a current will flow through inductor 1002 and switch 1003. This current will be low due to the self-inductance of inductor 1002 and then rise as the magnetic field builds up. According to the principles of inductors, when switch 1003 is opened the current through inductor 1002 remains constant, which means that the voltage can increase above the battery voltage if the connected resistance is high. This value of the voltage depends on the energy stored in inductor 1002 and therefore on how long switch 1003 was closed before it was opened. A capacitor 1004 smooths the voltage to largely eliminate any spikes from switching and a diode 1005 avoids reverse current from the capacitor 1004 into the inductor 1002. A Zener diode 1006 provides over voltage protection. This stops the output voltage from going too high and damaging components that have a stress limit e.g. when the load is accidentally disconnected. In this case this diode is connected to a small resistor R, 1007.

FIG. 11 illustrates the operation switch 1003 in the context of neural stimulation. Switch 1003 connects inductor 1002 to battery 901 for time $t_1$. Switch 1003 then connects inductor 1002 to tissue 1001 and current flows for a time $t_2$. Pulses are generated with a period $t_3$ and last for a period equal to the stimulus pulse width PW. The time $t_1$ controls how much energy is stored in the inductor. The problem of designing a useful current source consists of controlling these times in a useful manner. It is understood the time PW is simply the time the current source is enabled. The method to generate $t_1$, $t_2$ and $t_3$ is described below.

Once connected to the load, the inductor will pump charge into the load until it has no more energy to do so, and then due to the presence of diode 1005 the current will cease in a self-regulating manner. So the time $t_2$ is self-regulating. Energy Equations To appreciate how to control $t_1$, $t_2$ and $t_3$ in light of the requirements previously provided, it is useful to derive the equations of the switched mode charge pump of FIG. 10.

Assuming the charge pump cycle begins with zero current in inductor 1002, its current is given by:

$$I = \frac{Vt}{L}$$

11

12 where the voltage source voltage is V, the time the inductor is connected is t and the inductance is L. The identical equation describes the time taken for the inductor to dump all its power into a load, ending with the current in the inductor being zero. Thus, this equation applies to FIG. 10 with the switch in either position.

The energy stored by the inductor is $$E = \frac{L}{2} I^2$$

Substituting $$E = \frac{L}{2} \frac{V^2 t^2}{L^2} = \frac{1}{2L} V^2 t^2$$

Since energy is the product of power and time, and charge is the product of current and time:

$$E = V_1 I_1 t_1 = V_1 Q_1 = V_2 I_2 t_2 = V_2 Q_2$$

Although the time $t_1$ can be controlled, the time $t_2$ then depends on $V_1$ and $V_2$ in order to obey conservation of energy.

The charge delivered each cycle is:

$$Q_2 = \frac{E_2}{V_2} = \frac{V_1^2 t_1^2}{2L} \frac{1}{V_2}$$

And the average current delivered is $$I = \frac{E_2}{V_2} = \frac{V_1^2 t_1^2}{2L} \frac{f}{V_2}$$

Since $t_3$ is the reciprocal of f:

$$I = \frac{E_2}{V_2} = \frac{V_1^2 t_1^2}{2L} \frac{1}{t_3 V_2}$$

Since the charge delivered depends on $t_1$, $t_2$, $t_3$, $V_1$ and $V_2$, it is useful to provide a predictable average current and to eliminate these dependencies.

Circuitry

FIG. 12 illustrates a circuit component 1200 that can be used to achieve this in the sense that circuit component 1200 creates a time delay inversely proportional to a control voltage. This is called a "voltage controlled delay" (VCD) circuit and in this form it has two controls with the delay being proportional to the ratio of the two voltages. Circuit component 1200 comprises a capacitor 1201 that is discharged through a discharge transistor 1202 when a trigger signal 1203 connected to the base of discharge transistor 1202 goes high. A current mirror 1206 charges the capacitor 1201 by mirroring a reference current 1207 when the trigger signal 1203 goes low. This reference current 1207, in turn, is controlled by the second voltage $V_I$ 1208 amplified by amplifier 1209 which is buffered by buffer transistor 1210 including a negative feedback that ensures that the emitter voltage (i.e. the voltage across resistor 1211) is equal to $V_I$ 1208. As a result, reference current 1207 is $$I_{ref} = \frac{V_I}{R}.$$

In essence, if $V_I$ 1208 is high, a high reference current flows throw resistor 1211, leading to a high current into capacitor 1201 and a shorter time for charging capacitor 1201. Therefore, the delay for a rising edge is inversely related to $V_I$. The delay for a falling edge is determined by dimensions of transistor 1202, which can be chosen such that the delay for the falling edge is relatively short. In other words the falling edge is substantially instantaneous with a negligible delay caused by discharge transistor 1202. Conversely, a lower second voltage $V_I$ 1208 leads to a longer delay of the rising edge because the time to charge capacitor 1201 is longer. On the other hand, a high voltage for Vp 1205 leads to a longer delay since the voltage across capacitor 1201 needs to rise further before the output goes high. More formally, the general current voltage relation for capacitor 1201 is $$I = C \frac{dV}{dt}, \text{ so } dt = C \frac{dV}{I}.$$

Substituting the (constant) reference current yields $$dt = RC \frac{dV}{V_I}.$$

Considering that the required voltage difference to cause the output to switch is $dV = V_P$, the time from the trigger pulse going low to the response signal going high is $$t = RC \frac{V_P}{V_I}$$

In this, $V_P$ is considered the proportional control voltage and $V_I$ is the inverse control voltage.

In order to use component 1200 to generate the time $t_1$ the battery voltage is used as the inverse control $V_1$ 1208 and the proportional control voltage is kept constant. The result is for some constant a:

$$a = V_1 t_1$$

with $a = RCV_P$. The variation of energy in the inductor due to the varying battery voltage is hence eliminated.

To control the average current the situation is more complicated. It is desirable to increase the inductor energy to compensate for the decreased charge that is delivered as the load voltage increases. At the same time it is necessary to provide current control for the clinician, patient and the control loop. This control signal is digital.

FIG. 13 illustrates a digital controlled resistor circuit 1300 comprising four resistors 1301, 1302, 1303, 1304 and corresponding switches 1311, 1312, 1313, 1314. In this example, each resistor has a resistance that is double the resistance of the next smaller resistor similar to a binary number system. Each switch is controlled by one bit in a digital control signal M 1320. As a result, the overall resistance of the resistor circuit 1300 is set by the digital signal M 1320 such that each bit in M reduces the overall resistance by adding a parallel path. When resistor 1211 in FIG. 12 is now replaced by controlled resistor circuit 1300, the reference current 1207 increases with each active bit in M, which in turn decreases the charge time of capacitor 1201 decreasing delay $t_1$ which leads to a shorter charge time of inductor 1002 in FIG. 10 which finally leads to a decreased stimulation current.

Since the resistance is a multiplicative term in the expression above, the resulting circuit with controlled resistor circuit 1300 replacing resistor 1211 is referred to as "multiplying VCD" (MVCD) which multiplies the compensating term from the load voltage and the digital control. So, the MVCD has three inputs, Vi, Vp and M.

FIG. 14 illustrates a control circuit 1400 which implements the feedback circuit 904 in FIG. 9. The control circuit 1400 comprises an MVCD 1401 as shown in FIG. 12 but with the digitally controlled resistor circuit 1300 from FIG. 13 in place of resistor 1211. Control circuit 1401 further comprises a VCD 1402 as shown in FIG. 12. A feedback loop 1403 including an inverter 1404 causes an intermediate signal 1405 to oscillate and the oscillation frequency depends on the delay created by MVCD 1401 and generates the time $t_3$ where the pump output $V_2$ (voltage across switch 1003 in FIG. 10) is connected as the inverse control voltage $V_1$. VCD 1402 is used with V (battery voltage) as its inverse control, we can write, for some constant b of the second VCD circuit:

$$t_3 = b\frac{V_1}{V_2}.$$

Then $$I = \frac{a^2}{2L}\frac{V_C}{b}$$

At this point we have a current source that is controllable. The time between rising edges is controlled by Out of Compliance Circuit It is desirable that a clinician can detect when a current source goes out of compliance. In this case, this occurs when the shunt voltage regulator 1006 of FIG. 10 starts to conduct. A monitor on the resistor R, 1007 achieves this.

Design Range of First VCD

In the case where the battery voltage varies from 4.2V to 3.25V (a typical range for a lithium-ion rechargeable cell) the value of $t_1$ varies over a range of 1.29:1. This is a small range and so the design of the $t_1$ VCD is not problematic. This leaves room for additional control for the overall feedback and clinician control.

The V, inputs to the two VCDs are unused. They could be controlled by DACs to provide different current ranges. The range from 50 uA to 12.5 mA varies by 1:250. The load can vary from 1V to 15V, so the total variation is greater than 1:3750. If the PW=100 us, then the required resolution is 26 ns. This is technically difficult. The $V_P$ inputs provide additional degrees of freedom to span this space.

Design Range of Second VCD

A solution to this problem is to waste a bit of voltage in the load as shown in FIG. 15. The cascode p-channel FET 1501 limits the load voltage to the sum of the voltage $V_L$ plus the p-FET turn on voltage 0.6V, at small values of the load impedance or small currents. At higher impedances, the load voltage becomes larger and in the limit the FET drain-source voltage tends to zero and the FET becomes a small parasitic resistance in the current delivery chain. This modification will limit the battery life improvements for patients who have comparatively low tissue impedances, but there will still be considerable improvement compared to the alternative of dissipating power in the current source transistor.

Depending on the load, the voltage $V_2$ can vary between the maximum the circuitry can withstand and where the Zener diode turns on (at say 16.5V) to the sum of the p-FET source voltage when there is a zero ohm load plus the diode voltage. Since $V_L$ is under the control of the designer this can be arbitrarily chosen; a value of 5V would be suitable. In this instance the voltage $V_2$ would vary from 16.5V to 5V i.e. a range of 3.3. Again, there is room to incorporate additional control.

FIGS. 16 and 17 show examples of a digitally controlled resistance or conductance, respectively. Observing that FIG. 14 has two resistors (one in MVCD 1401 and one in VCD 1402) and either can be a controlled resistance or a controlled conductance, and one appears in the numerator and one in the denominator of the current equation, then there are a lot of options. Now these can be placed in the R spot, or driven with a current source to provide the proportional and inverse inputs.

The DAC

FIG. 18 illustrates a deterministic way of combining two amplitude controls in a pulse modulation system. It is also possible to use random values as per a delta-sigma DAC.

Example Numeric Values

Inverting the equation $$I = \frac{E_2}{V_2} = \frac{V_1^2 t_1^2}{2L}\frac{1}{t_3 V_2}$$

we get $$L = \frac{E_2}{V_2} = \frac{V_1^2 t_1^2}{2I}\frac{1}{t_3 V_2}$$

Substituting $V_1$=3.25, $t_1$=500 ns, I=12.5 mA, $t_3$=1 us, $V_2$=15V gives L=7 uH.

This provides 1 us per pulse (0.5 us to charge the inductor, 0.5 us to dump it), so in a 100 us stimulus pulse, we have about 6.5 bits of control. However, a feedback term and clinician term may need to be included.

FIG. 19 illustrates another example for a device 1900 for applying a neural stimulus. In this example, device 1900 comprises a battery 1901 to supply electrical energy at a battery voltage and a fixed current source 1902 powered by battery 1901. The fixed current source 1902 is fixed in the sense that it is set at a relatively high current. For example, the current may be set at a maximum value and then modulate the pulse width. Or there may be coarse control of current by the clinician, setting it at approximately at the expected or estimated maximum required for that patient. While this current source can be implemented with a current mirror, it is noted that keeping the current fixed at a relatively high current or maximum current, reduces the voltage drop across the current mirror and therefore reduces the power dissipated in the current mirror.

Device 1900 further comprises a pulse generator 1903 that is connected to an electrode selector 1904 controlled by an electrode selection signal 1905 (set by the clinician). The electrode selector 1904 selects from multiple electrodes a stimulation electrode 1906 to apply the electrical energy to neural tissue 1907, return electrode 1908, measurement (sense) electrode 1909 and reference electrode 1910.

Device 1900 further comprises a differential amplifier 1911 that amplifies the signal captured by sense electrode 1909 and provides that to a correlator 1912 to calculate an ECAP amplitude 1913 as described above with reference to FIG. 5. In the example of FIG. 19, the ECAP amplitude is again the input to a feedback control circuit 1914, which calculates a pulse width 1915 provided to the pulse generator 1903. In this sense, the feedback control circuit 1914 increases the pulse width to provide more stimulation energy when the ECAP amplitude is below a desired value and decreases the pulse width when the ECAP amplitude is above a desired value. For example, a switched-mode converter with a current or voltage output may be configured to provide a fixed amplitude output, with the pulse width being varied to provide the stimulus variation needed for a closed loop stimulation system.

FIG. 20 illustrates the manner in which a stimulus 2001 produces an ECAP 2002, which is then aligned with a template 1916 to provide amplitude measurement in the manner described in US20160287182 and with reference to FIG. 5, which is included in its entirety herein by reference.

As nerve cells are mostly triggered throughout the duration of the cathodic phase of the stimulus pulse, when feedback control circuit 1914 changes the pulse width 1915 provided to the pulse generator 1930, the time between the start of the stimulus and the arrival of response at the recording electrodes varies. The time of arrival of the ECAP 2002 can be measured as the time to the arrival of the first peak of the ECAP, the P1 peak, although other features may also be used. In order for the detector/correlator 1912 to work properly, the detector template is aligned to be synchronous with the ECAP a during the detection process.

One example of aligning the template 1916 involves a lookup table 1917 which indicates the optimum delay between the stimulus and the detection process for that particular pulse width. This optimum delay is then fed to a variable delay circuit 1918, which might be a variable-length shift register, to trigger the correlator, which determines the ECAP amplitude as per US20160287182 and shown in FIG. 5 above.

As a result, the device 1900 generates stimulation current pulses and adjust the pulse length of the current pulses based on the measured nervous response of the tissue to reduce the dissipated power, while at the same time aligning the template to the ECAP signal to accurately measure the ECAP amplitude that is used for the feedback control that ultimately controls the width of the stimulation pulses.

In one example, the pulse width is controlled digitally by a microprocessor. As a result, the pulse width has a limited number of different values, such as 256 different values for an 8-bit pulse width signal. In that case, the lookup table may have 256 different delay values, which is one delay value for each pulse width value. The delay values may be in the form of counter values for an internal processor counter to reach the counter value before the template signal is generated. In other examples, the pulse width is continuous, such as a float number or an analogue signal and the look-up table stores 256 values. The variable delay 1918 module may then interpolate between the closest values in the lookup table 1917 to determine the optimum delay. The look-up table 1917 may be replaced by a functional approximation of the relationship between the pulse width and the template delay, such as a linear function with two parameters or a polynomial with further parameters.

It is noted that the variable pulse width control described with reference to FIG. 19 may be combined with the switched-mode current source of FIG. 10 potentially including the circuits from FIGS. 13, 16 and 17. In that case and referring back to FIG. 11, the resulting circuit would control $t_1$ and $t_3$ as well as the pulse width PW to adjust the stimulation level. However, in other examples, the circuit maintains $t_1$ and $t_3$ constant and only adjusts PW.

FIG. 21 illustrates a further example where the feedback control is implemented directly in the converter, and avoids the use of a sub-regulator. In particular, FIG. 21 illustrates an implantable stimulation device 2100 comprising a battery 2101, a switched-mode power supply (SMPS) converter 2102, an H-bridge drive 2103 and an output electrode 2104 to supply an electrical stimulus to nervous tissue. There is also a sense electrode 2105 to capture an evoked response and a feedback circuit 2106. Importantly, the feedback circuit 2106 is now connected directly to the converter 2102.

When the converter is a voltage-to-current converter, the operation is as discussed above. If the converter is voltage-to-voltage, then this an introduction to subsequent sections of this document.

The stimulator described below provide most of the benefits of voltage drive, while fitting within the framework of existing clinical systems and may be preferred amongst the variants mentioned in this disclosure.

FIG. 22 illustrates a further example stimulation device 2200 comprising a battery 2201, a voltage-to-voltage SMPS converter 2202 connected to a sub-regulator 2203 (similar to the current mirror in the previous figures) and a smoothing capacitor 2204. The sub-regulator 2203 mirrors a control current 2205 to an H-bridge drive 2206 which, in turn, delivers the current to a stimulation electrode output 2207. A sample and hold circuit 2208 samples the stimulation voltage and a sense electrode 2209 senses the evoked response, which is amplified by an amplifier 2210. The signals from amplifier 2210 and sample and hold circuit 2208 are selectively switched by a switch 2211 onto an analog-to-digital converter 2212 that converts the selected signal to a digital input of a digital controller 2213. The controller 2213 can then use the sampled stimulation output voltage and the sensed evoked response to calculate a control current of current source 2214 and a control voltage for converter 2215. Both are provided by respective digital-to-analog converters 2214, 2215. It is noted that the DACs 2214, 2215 and ADC 2212 may be integrated into the digital controller 2213.

This design moves the SMPS control loop into digital controller 2213. The peak stimulus voltage is obtained by sample circuit 2208 sampling the stimulus electrode at the end of the stimulus. This can be held in the sample-hold circuit 2208, and converted to a digital value in the ADC 2212. This ADC 2212 can be the same one used for digitizing the physiological feedback. Since the digital controller 2213 will also be used to operate the physiologic control loop, it will have available the stimulus amplitude used for the next stimulus, and, via the digital control of the SMPS 2202, can prepare the power supply for the next stimulus i.e. use feed-forward in the loop. The sample rate is typically 60 Hz for many neuro-modulation applications, so the SMPS 2202 has more than 10 ms to respond to the updated control voltage, making it a simpler design than that of FIGS. 7 and 8 which respond during the stimulus.

The digital controller 2213 can be a programmable micro-controller or a dedicated state-machine.

FIG. 23 illustrates a voltage-drive version of FIG. 22. Again, there is a battery 2301, a voltage-to-voltage converter 2302, an H-bridge 2303 connected to a stimulation electrode 2304. There is also a sense electrode 2305 connected to an amplifier 2306 and a switch 2307 that selectively connects the voltage from the converter 2302 or from amplifier 2306 to an ADC 2308 connected to controller 2309. The controller calculates the control voltage for converter 2302, which is provided through DAC 2310 on an analog control voltage signal 2311. While the components shown in FIG. 23 are similar to those in FIG. 22, in FIG. 23 there is no sub-regulator 2202 as in FIG. 22. Instead, the converter 2302 delivers the voltage directly to the stimulus output 2304 (via H-bridge 2303). "Directly" in this context means without further voltage or current control since the H-bridge 2303 is only a connection circuit with no regulating function. In other words, the switches in H-bridge drive 2303 remain unchanged (on or off) during stimulation, while the switches in converter 2302 change many times to control the voltage.

It is noted that most available converters that can be used as SMPS 2302 have a feedback input to feedback the voltage at their output. This feedback input is now used in FIG. 23 to provide the control voltage signal 2311 to converter 2302. The main difference to the common use case of closed-loop wired voltage feedback is that the feedback signal 2311 is now generated by digital controller 2309. This way, controller 2309 can control the converter 2302 by adjusting the voltage on control signal 2311. In one example, digital controller 2309 sets the control signal 2311 to a voltage level that is the desired voltage. However, there may be a difference, such as an offset between the desired output voltage and the control voltage 2311 if the converter 2302 includes a scale factor or offset due to varying battery voltage, for example.

With this implementation, controller 2309 can monitor the output voltage of the power supply to detect any over-voltage or to detect that despite the maximum voltage has been applied there is little increase in the physiological response. Further, controller 2309 receives the feedback signal from amplifier 2306 and can compare it to a desired value. Controller 2309 can then perform a control algorithm, such as PID, to reduce the difference between the measure and the desired evoked response by varying the output signal provided to DAC 2301. This may result in improved dynamic characteristics of converter 2302, such as settling time and ringing, compared to direct voltage feedback through analog comparison with a reference voltage. It also reduces the need for analog components with are often a source of fluctuation and other implementation difficulties. It is noted that DAC 2310 may also be integrated into converter 2302 in the sense that converter 2302 is configured to accept a digital signal and to control the output voltage accordingly.

In one example, converter 2302 is a ringing choke converter comprising primary and secondary windings of a transformer and a base winding on the primary side. A transistor is connected to the base winding so that a self-oscillation occurs in the primary side and at each oscillation the transistor switches. This oscillation results in an induced current in the secondary side, which can be smoothed by a transistor into a DC signal. Importantly, the switching frequency depends on the input voltage and the state of the load. Now, the digital controller 2309 controls that input voltage via voltage signal 2311 and therefore, controls the switching frequency in converter 2302. In turn, this controls the output voltage of converter 2302 and finally the stimulation intensity on electrode 2304. As described herein, the controller 2309 adjusts the voltage on control signal 2311 based on the physiological input.

FIG. 24 illustrates a further implementation of an implantable stimulation device 2400 where, compared to FIG. 23, the DAC 2310 is omitted and the controller 2309 directly provides the timed pulses for the switching in switched-mode power supply converter 2302 through a pulse width modulation output 2410. In particular, controller 2309 generates arbitrary waveforms. It is noted that many microcontrollers already provide the functionality of a pulse width modulation (PWM) control output. Therefore, processor 2404 may be a general purpose microcontroller or other processor circuit, such as an FPGA or ASIC.

The duty cycle (ratio between ON and OFF), as defined by the PWM signal, defines the voltage of the output signal. This means that a change in the conductance of the neural tissue is automatically compensated in the sense that a lower conductance leads to a higher voltage to achieve the same evoked response.

More particularly, there may be two control loops. A first control loop controls the output voltage while a second control loop controls the evoked neural response. In one example, the first control loop is repeatedly executed during the application of a stimulation pulse. A desired output voltage is stored in digital controller 2309 and during the stimulation, the controller 2309 compares the present voltage (provided through switch 2307) to the desired voltage. If there is a difference, controller 2309 adjusts the duty cycle, such that the duty cycle is increased if the output voltage is less than the desired voltage and vice versa. The second control loop is executed once per stimulation phase, where the desired output voltage is adjusted based on a comparison between a desired evoked response and the measured evoked response. For example, controller 2309 increases the desired output voltage if the measured evoked response is below the desired evoked response and vice versa. Then, the desired voltage is used in the first control loop during the next stimulation phase. Known topologies for buck-boost converters include SEPIC and Cúk topologies.

FIG. 29 illustrates a method 2900 for neural stimulation. The method comprising repeatedly performing the following steps in the sense that the following steps are repeated to provide continuous stimulation by multiple stimulation pulses. So in one example, method 2900 is performed once for each stimulation pulse.

The method 2900 commences by generating 2901 a stimulation voltage signal at a stimulation voltage, such as by switching a switched-mode power supply. Next, the stimulation voltage signal is applied 2902 to neural tissue. A measurement circuit then measures 2903 a nervous response of the tissue. Finally, the stimulation voltage is adjusted 2904 based on the measured nervous response.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A device for applying a neural stimulus comprising:
a battery to supply electrical energy at a battery voltage;
an electrode to apply the electrical energy to neural tissue;
a circuit to measure a nervous response of the neural tissue;
a switched mode voltage to current converter to receive the electrical energy from the battery and to control a current applied to the electrode; and a controller configured to control switching of the switched mode voltage to current converter based on the measured nervous response of the neural tissue.

2. The device of claim 1, wherein the controller is further configured to control the switching based on the battery voltage.

3. The device of claim 1, wherein the controller is further configured to control the switching based on an electrode voltage.

4. The device of claim 1, wherein the controller is further configured to control the switching based on a predetermined stimulation intensity.

5. The device of claim 1, wherein the controller comprises a pulse generator to generate a pulse signal to control the switching.

6. The device of claim 5, wherein the pulse generator comprises a voltage controlled oscillator to generate the pulse signal.

7. The device of claim 5, wherein the controller comprises a voltage controlled oscillator to control a frequency of the pulse signal based on a desired level of stimulation and a tissue voltage and a voltage controlled delay to control a time period for which a switch connects an inductance to the battery at each oscillation based on the battery voltage.

8. The device of claim 5 wherein the pulse signal is periodic and controlling the switching comprises suppressing pulses that turn a switch on to set the amount of energy provided by an inductance.

9. The device of claim 1, wherein the controller comprises a voltage controlled delay controlled by the battery voltage to control the switching.

10. The device of claim 9 wherein the voltage controlled delay is connected to a switch to disconnect an inductance from the battery after a delay controlled by the battery voltage.

11. The device of claim 9, wherein the voltage controlled delay is connected to a switch to disconnect an inductance from the battery after a delay controlled by a tissue voltage.

12. The device of claim 9, wherein the voltage controlled delay is connected to a switch to disconnect an inductance from the battery after a delay controlled by a desired level of stimulation intensity.

13. The device of claim 1, wherein the controller is a digital processor.

14. The device of claim 13, wherein the device comprises an analog-to-digital converter to provide a digital signal indicative of the measured nervous response of the neural tissue to the digital processor.

15. A device for applying a neural stimulus comprising:
  a battery to supply electrical energy at a battery voltage;
  an electrode to apply the electrical energy to neural tissue;
  a circuit to measure a nervous response of the neural tissue; and
  a pulse generator to generate stimulation current pulses at a pulse length and to adjust the pulse length based on the measured nervous response of the neural tissue;
  wherein the circuit to measure the nervous response of the neural tissue comprises a template and the circuit is configured to shift the template in time relative to the stimulation current pulses based on the pulse length so as to measure the nervous response of the neural tissue.

16. The device of claim 15, wherein the circuit comprises a look-up table storing delay values for the template for each of multiple pulse width values.

* * * * *